US011224487B2

(12) United States Patent
Canady et al.

(10) Patent No.: US 11,224,487 B2
(45) Date of Patent: Jan. 18, 2022

(54) ROBOTIC SURGICAL SYSTEM

(71) Applicant: U.S. Patent Innovations, LLC, Takoma Park, MD (US)

(72) Inventors: Jerome Canady, Lakeland, FL (US); Cheffren Canady, Washington, DC (US); Taisen Zhuang, Rockville, MD (US); Feng Yan, Fairfax, VA (US); Aditya Shanghavi, Silver Spring, MD (US); Zhangshi Liu, Silver Spring, MD (US); Daniel Tabatabai, Annandale, VA (US); Tanner Pierce, Washington, DC (US)

(73) Assignee: US Patent Innovations, LLC, Takoma Park, MD (US)

( * ) Notice: Subject to any disclaimer, the term of this patent is extended or adjusted under 35 U.S.C. 154(b) by 667 days.

(21) Appl. No.: 15/577,984

(22) PCT Filed: Sep. 25, 2017

(86) PCT No.: PCT/US2017/053341
§ 371 (c)(1),
(2) Date: Nov. 29, 2017

(87) PCT Pub. No.: WO2018/058079
PCT Pub. Date: Mar. 29, 2018

(65) Prior Publication Data
US 2019/0090963 A1    Mar. 28, 2019

Related U.S. Application Data

(60) Provisional application No. 62/399,332, filed on Sep. 23, 2016.

(51) Int. Cl.
*A61B 34/30*     (2016.01)
*A61B 34/00*     (2016.01)
(Continued)

(52) U.S. Cl.
CPC ............. *A61B 34/30* (2016.02); *A61B 17/29* (2013.01); *A61B 17/3201* (2013.01);
(Continued)

(58) Field of Classification Search
CPC ............ A61B 17/29; A61B 17/320016; A61B 17/3201; A61B 17/3476; A61B 17/3478;
(Continued)

(56) References Cited

U.S. PATENT DOCUMENTS 6,312,435 B1   11/2001   Wallace et al.
6,783,524 B2    8/2004   Anderson et al.
(Continued)

FOREIGN PATENT DOCUMENTS

WO    2014134031 A2    2/2014
WO    2014134023 A1    4/2014
WO    2016057225 A1    4/2016

OTHER PUBLICATIONS

Haibo Yu, Liao Wu, Keyu Wu and Hongliang Ren, "Development of a Multi-Channel Concentric Tube Robotic System With Active Vision for Transnasal Nasaopharyngeal Carcinoma Procedures", IEEE Robotics and Automation Letters, vol. I, No. 2, Jul. 2016.

*Primary Examiner* — Alexander J Orkin
(74) *Attorney, Agent, or Firm* — 24IP Law Group USA, PLLC; Timothy DeWitt

(57) ABSTRACT

A robotic surgical system and accessory having a robotic base or hand piece having a plurality of motors and a mechanical actuator each for operating a mechanical positioning arm in a different degrees of freedom. The robotic base is reusable and provides the platform for the system. The drive system has a port that interfaces with the robotic base and allows for insertion of surgical instruments into the base.

10 Claims, 42 Drawing Sheets

(51) Int. Cl.
*A61B 17/29* (2006.01)
*A61B 17/32* (2006.01)
*A61B 17/3201* (2006.01)
*A61B 17/34* (2006.01)
*B25J 9/00* (2006.01)
*B25J 11/00* (2006.01)
*A61B 17/00* (2006.01)

(52) U.S. Cl.
CPC .. *A61B 17/320016* (2013.01); *A61B 17/3476* (2013.01); *A61B 17/3478* (2013.01); *A61B 34/74* (2016.02); *B25J 9/0009* (2013.01); *B25J 11/008* (2013.01); *A61B 2017/00398* (2013.01); *A61B 2017/2902* (2013.01); *A61B 2017/2908* (2013.01); *A61B 2017/2927* (2013.01); *A61B 2017/2936* (2013.01); *A61B 2017/2939* (2013.01); *A61B 2034/301* (2016.02); *A61B 2034/742* (2016.02)

(58) Field of Classification Search
CPC .. A61B 2017/00398; A61B 2017/2908; A61B 2017/2927; A61B 2017/2936; A61B 2017/2939; A61B 2034/301; A61B 2034/742; A61B 34/30; A61B 34/74; B25J 11/008; B25J 9/0009
See application file for complete search history.

(56) References Cited

U.S. PATENT DOCUMENTS

| | | | |
|---|---|---|---|
| 8,800,838 B2* | 8/2014 | Shelton, IV | A61B 17/115 227/175.1 |
| 9,360,934 B2 | 6/2016 | Ruiz et al. | |
| 9,386,983 B2 | 7/2016 | Swensgard et al. | |
| 9,398,911 B2 | 7/2016 | Auld | |
| 2006/0276775 A1* | 12/2006 | Rosenberg | A61B 17/00234 606/1 |
| 2008/0308607 A1 | 12/2008 | Timm et al. | |
| 2013/0197543 A1* | 8/2013 | Bonutti | A61B 17/1757 606/130 |
| 2014/0025089 A1 | 1/2014 | Sholev | |
| 2014/0246471 A1* | 9/2014 | Jaworek | A61B 17/068 227/175.1 |
| 2014/0305989 A1* | 10/2014 | Parihar | A61B 17/0686 227/176.1 |
| 2015/0080907 A1* | 3/2015 | Herrell | A61B 1/00133 606/130 |
| 2016/0157945 A1 | 6/2016 | Madhani et al. | |
| 2018/0049822 A1* | 2/2018 | Henderson | A61B 34/30 |

* cited by examiner

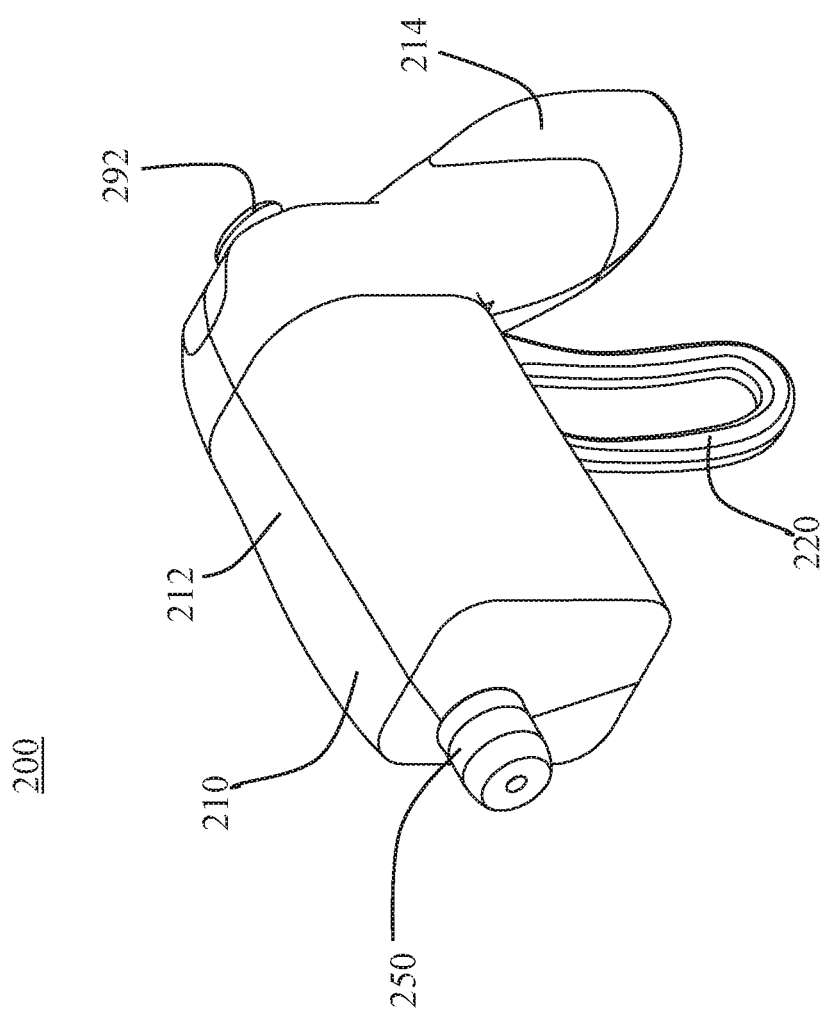

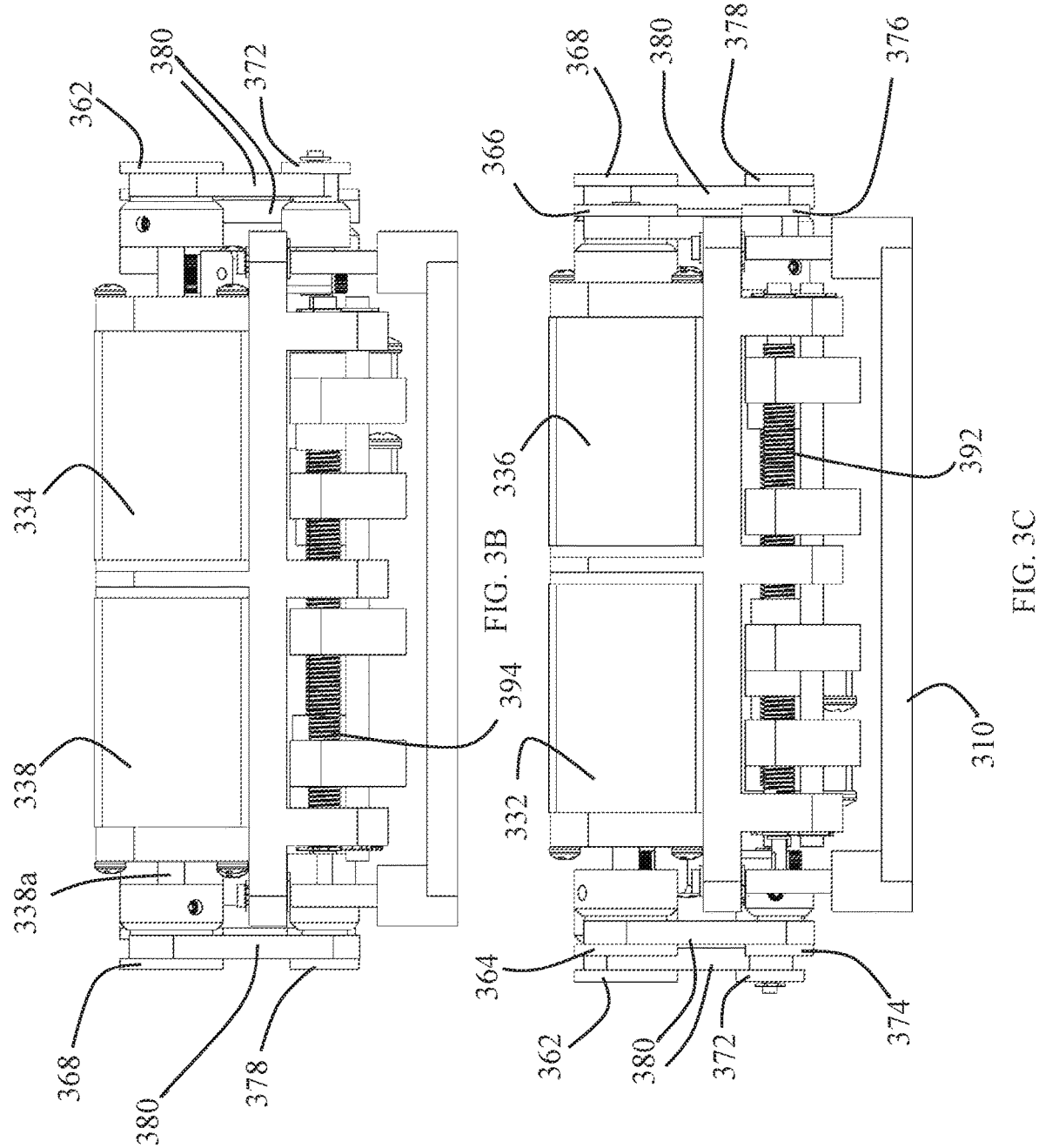

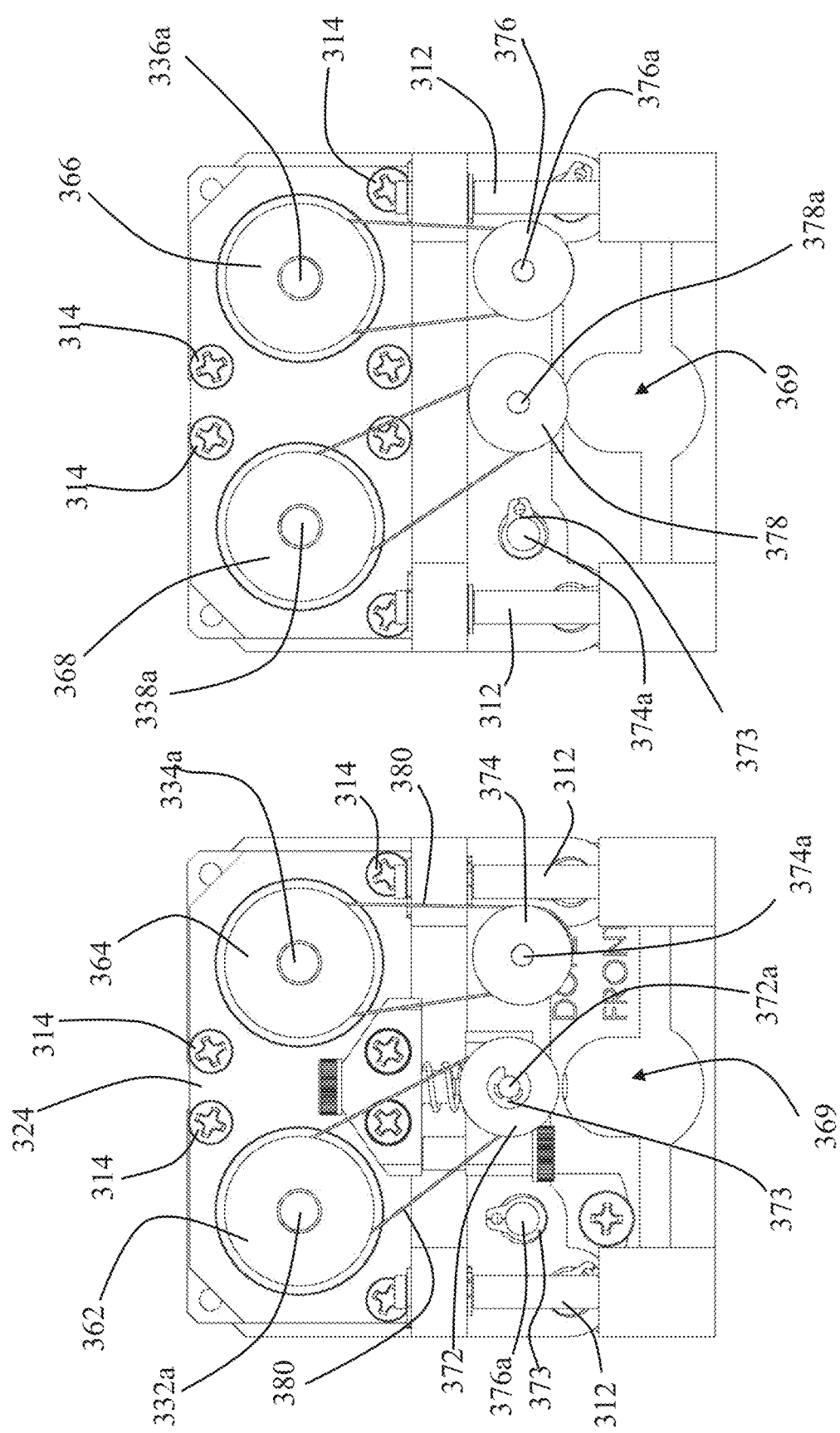

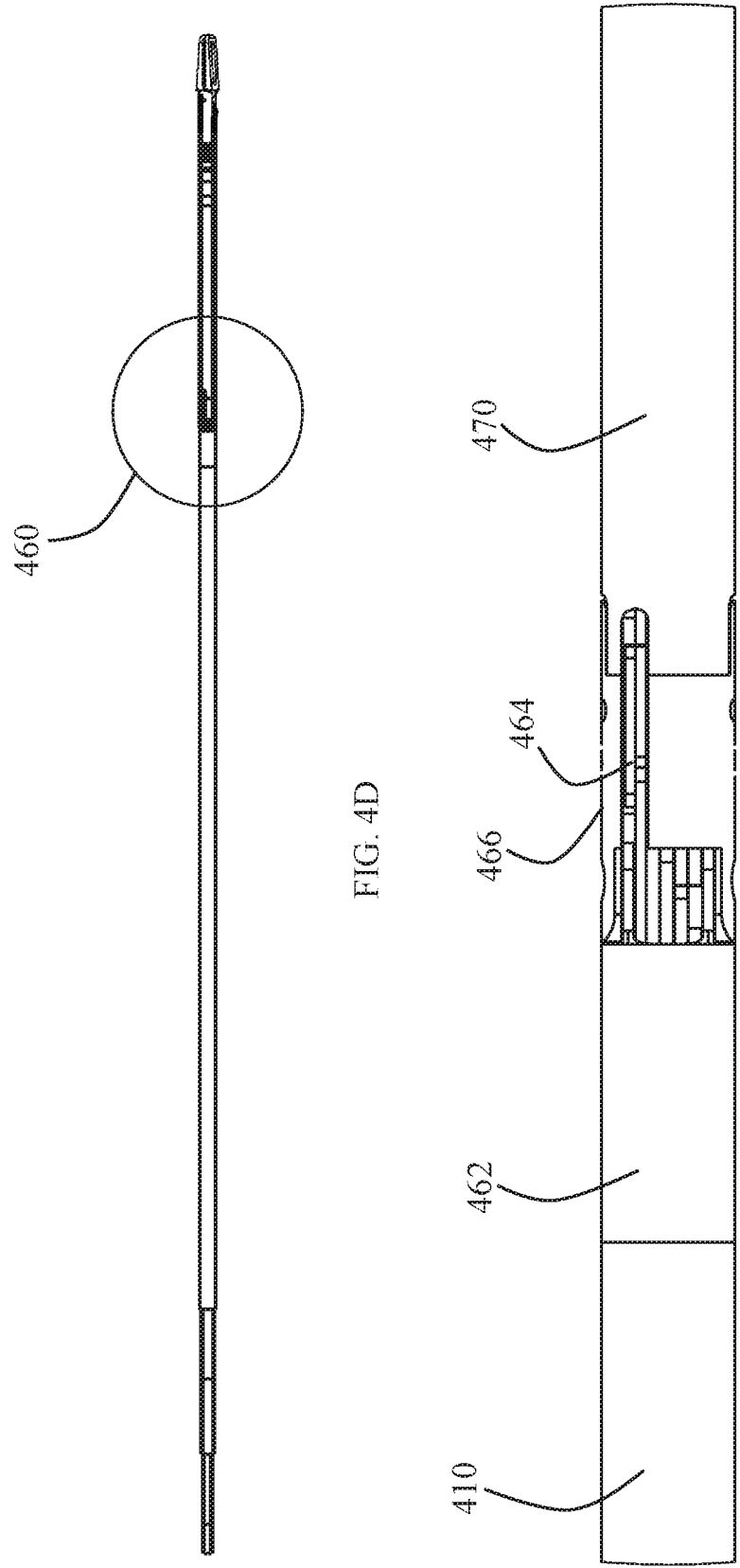

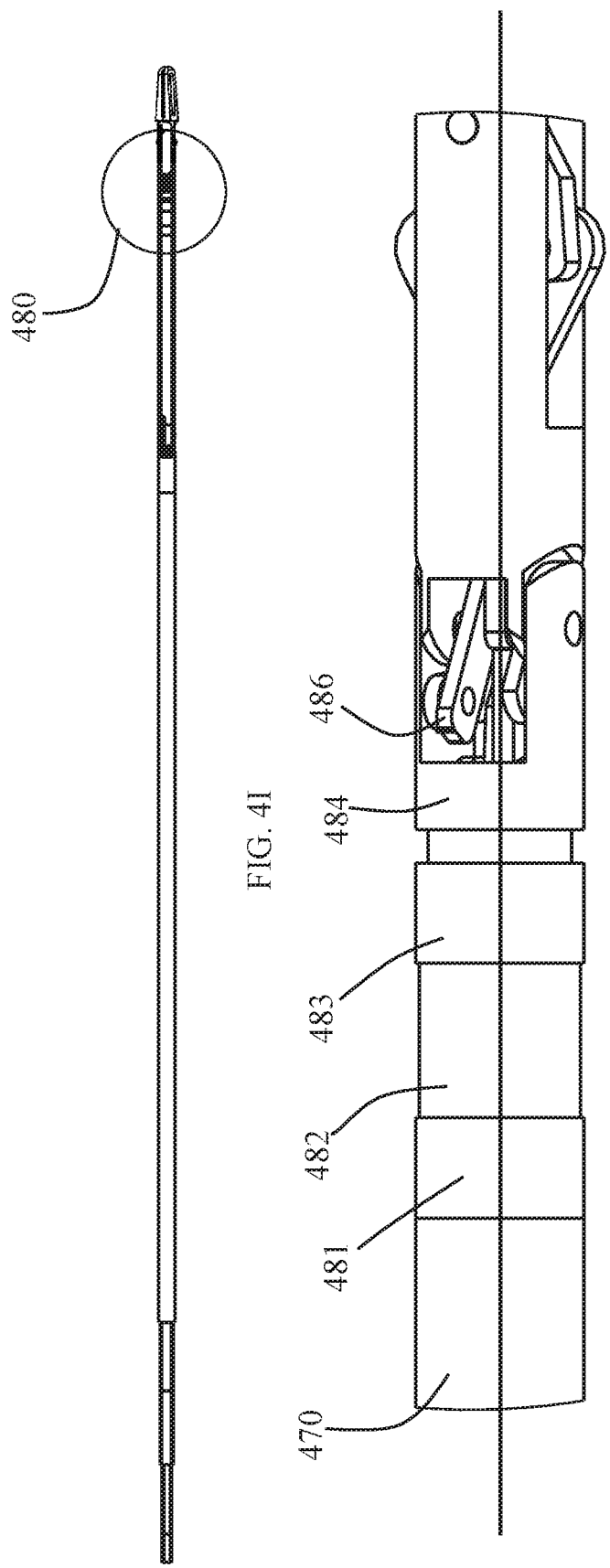
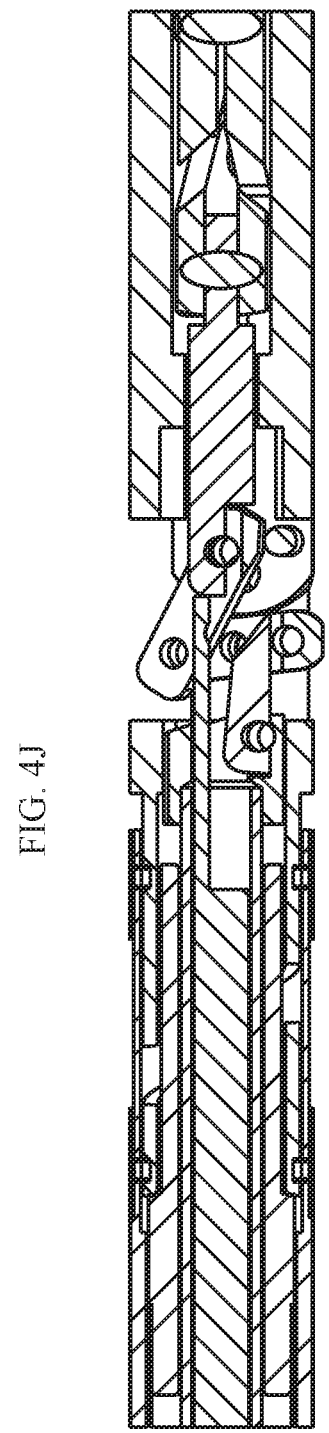
FIG. 4I
FIG. 4J
FIG. 4K

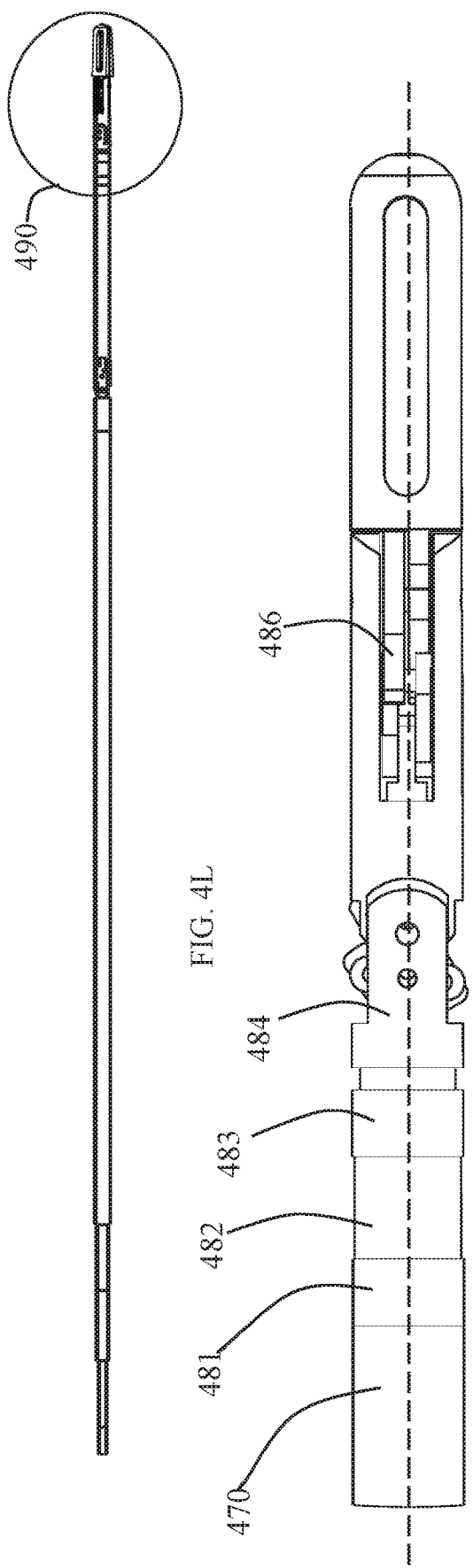
FIG. 4L
FIG. 4M
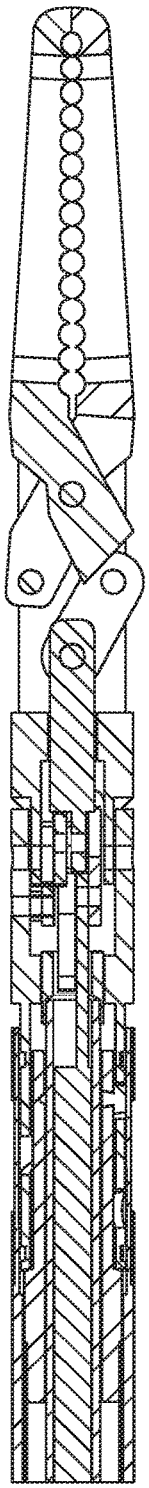
FIG. 4N

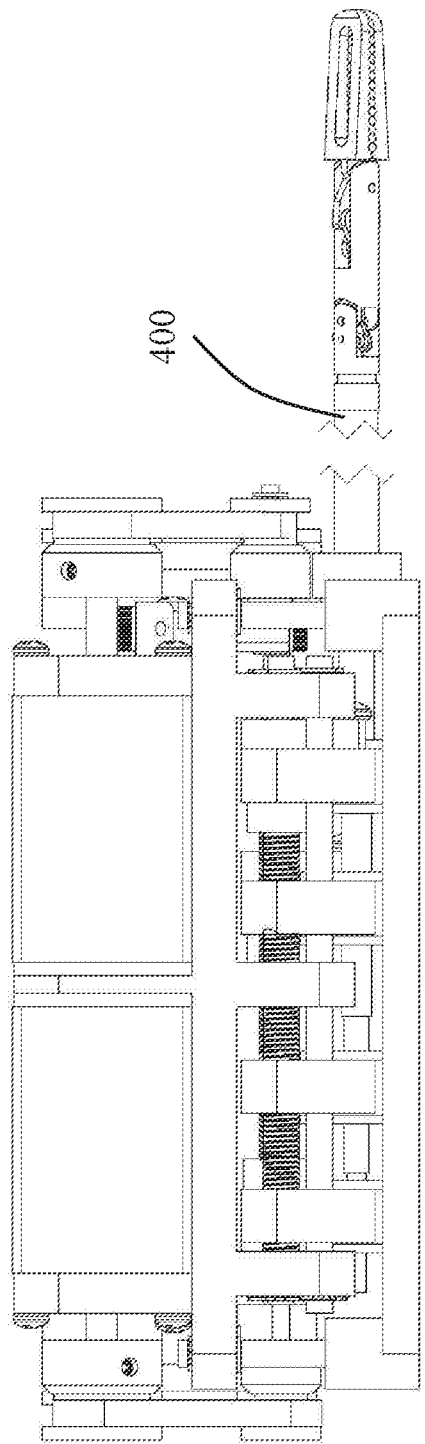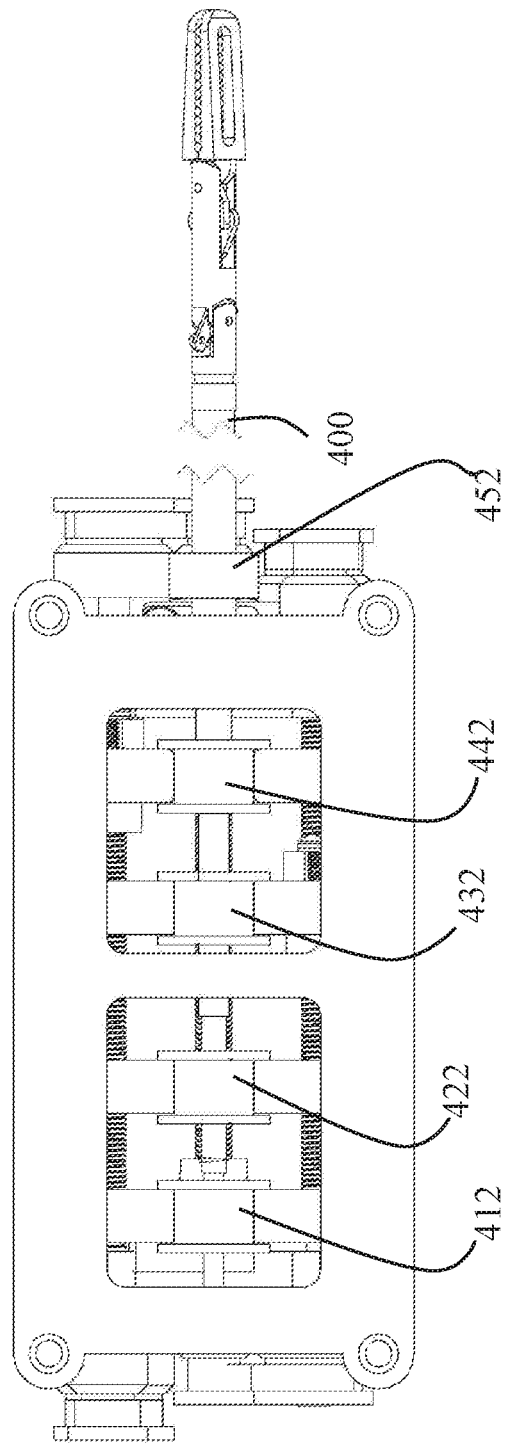
FIG. 5C
FIG. 5D

ROBOTIC SURGICAL SYSTEM

CROSS-REFERENCE TO RELATED APPLICATIONS

The present application claims the benefit of the filing date of U.S. Provisional Patent Application Ser. No. 62/399,332 filed by the present inventors on Sep. 23, 2017.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to robotic surgical systems and accessories for performing surgery.

Brief Description of the Related Art

In the last twenty years laparoscopic surgery has evolved as a less invasive alternative to open surgery. Millions of laparoscopic surgical procedures are performed each year worldwide. A laparoscopic or thoracoscopic surgical procedure is performed by creating multiple small one inch incisions throughout the abdominal wall or chest wall respectively. A pneumoperitoneum is created by the infusion of carbon dioxide gas to provide visualization and working space in the abdominal cavity. Flexible or rigid instruments are introduced through ports placed in the incisions to perform surgical tasks. Despite the broad acceptance there are limitations using a rigid laparoscope which creates difficult angles, causing the surgeon to hold instruments in a fixed positions for a substantial periods of time. Another challenge with the rigid laparoscope is the inadequate motions the surgeon can perform to reach potential defects or tumors of the abdominal wall as well as the inability to perform internal articulation.

There has been a worldwide acceptance of robotic-assisted surgery. Despite the advances in robotic surgery there are limitations to systems such as are disclosed in U.S. Pat. Nos. 6,312,435 and 6,783,524. For example, in those systems the robot requires the surgeon to sit outside the sterile field working at a large console. Another robotic system disclosed in U.S. Pat. No. 9,360,934 requires a large console place in the middle of the operating field. All of these systems depend on a multiple gear and cable system from their console to the flexible robotic instruments.

In addition to the robotic systems discussed above, several motorized surgical instruments have been proposed, for example in U.S. Pat. Nos. 9,386,983 and 9,398,911. In each of these systems, a motorized surgical stapler system is disclosed which provides a limited number of motorized degrees of freedom.

SUMMARY OF THE INVENTION

In a preferred embodiment, the present invention is robotic surgical system that provides five degrees of freedom through a single hand piece, motor assembly (or drive system) and arm assembly. The motor assembly has a single port that interfaces with a control unit and a port that allows for insertion of the proximal end of an arm assembly into the motor assembly. The arm assembly may have one or more surgical instruments at or near its distal end.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIG. 1I is a perspective view of the robotic surgical system of FIG. 1A illustrating ranges of motion of the arm assembly in accordance with a preferred embodiment of the present invention.

FIG. 2A is a perspective view of a housing of a robotic surgical system in accordance with a preferred embodiment of the present invention.

FIG. 3B is a first side view of a motor assembly of a robotic surgical system in accordance with a preferred embodiment of the present invention.

FIG. 3C is a second side view of a motor assembly of a robotic surgical system in accordance with a preferred embodiment of the present invention.

FIG. 3F is a front view of a motor assembly of a robotic surgical system in accordance with a preferred embodiment of the present invention.

FIG. 3G is a rear view of a motor assembly of a robotic surgical system in accordance with a preferred embodiment of the present invention.

FIG. 4D is a second side view of an arm assembly illustrating the first degree of freedom of a robotic surgical system in accordance with a preferred embodiment of the present invention.

FIG. 4E is a second side view of a first degree of freedom of an arm assembly of a robotic surgical system in accordance with a preferred embodiment of the present invention as shown in FIG. 4D.

FIG. 4I is second side view of an arm assembly illustrating the second degree of freedom of a robotic surgical system in accordance with a preferred embodiment of the present invention.

FIG. 4J is a second side view of the second degree of freedom of an arm assembly of a robotic surgical system in accordance with a preferred embodiment of the present invention as shown in FIG. 4I.

FIG. 4K is a second cross-section view of the second degree of freedom of an arm assembly of a robotic surgical system in accordance with a preferred embodiment of the present invention as shown in FIG. 4I.

FIG. 4L is side view of an arm assembly illustrating a third degree of freedom of a robotic surgical system in accordance with a preferred embodiment of the present invention.

FIG. 4M is a side view of the third degree of freedom of an arm assembly of a robotic surgical system in accordance with a preferred embodiment of the present inventions shown in FIG. 4L.

FIG. 4N is a cross-section view of a third degree of freedom of an arm assembly of a robotic surgical system in accordance with a preferred embodiment of the present invention as shown in FIG. 4L.

FIG. 5C is a first side view of a motor assembly with an arm assembly in accordance with a preferred embodiment of the present invention.

FIG. 5D is a top view of a motor assembly with an arm assembly in accordance with a preferred embodiment of the present invention.

DETAILED DESCRIPTION OF THE PREFERRED EMBODIMENTS

Figure 2B:
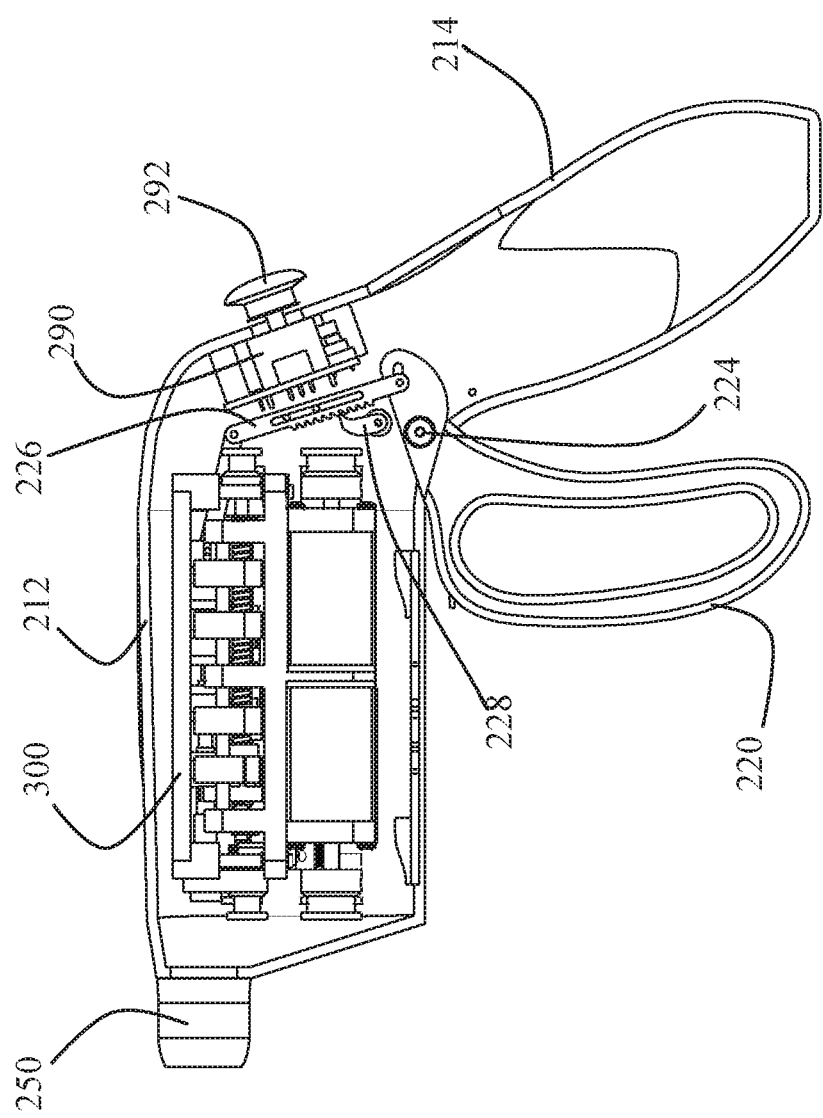
FIG. 2B is a first side view of the assemblies located within the housing in accordance with a preferred embodiment of the present invention.
Figure 2C:
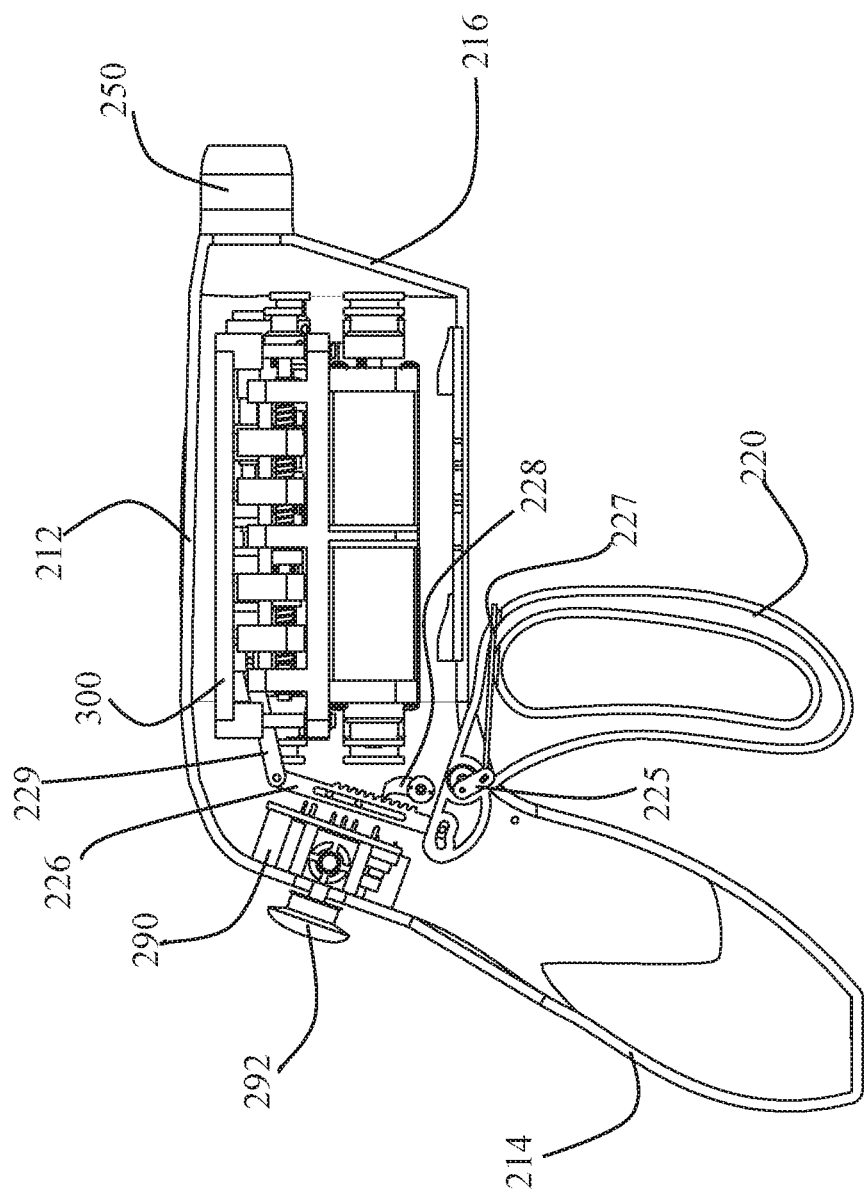
FIG. 2C is a second side view of the assemblies located within the housing in accordance with a preferred embodiment of the present invention.
Figure 2E:
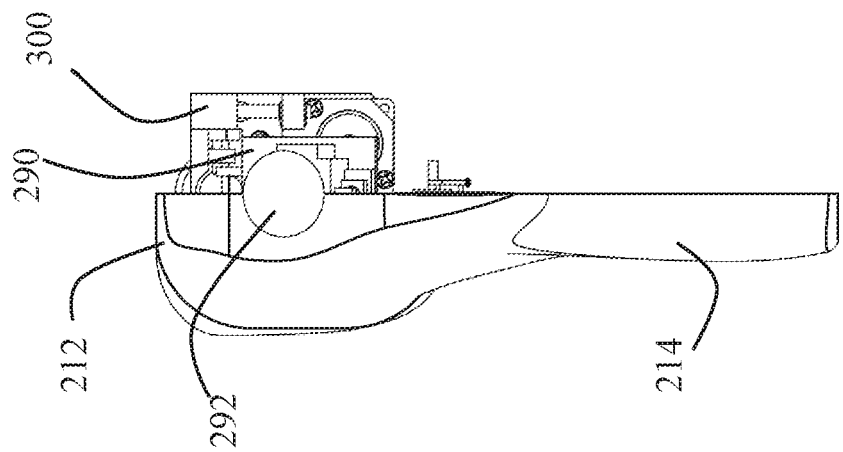
FIG. 2E is a rear end view of the assemblies located within the housing in accordance with a preferred embodiment of the present invention.
Figure 2D:
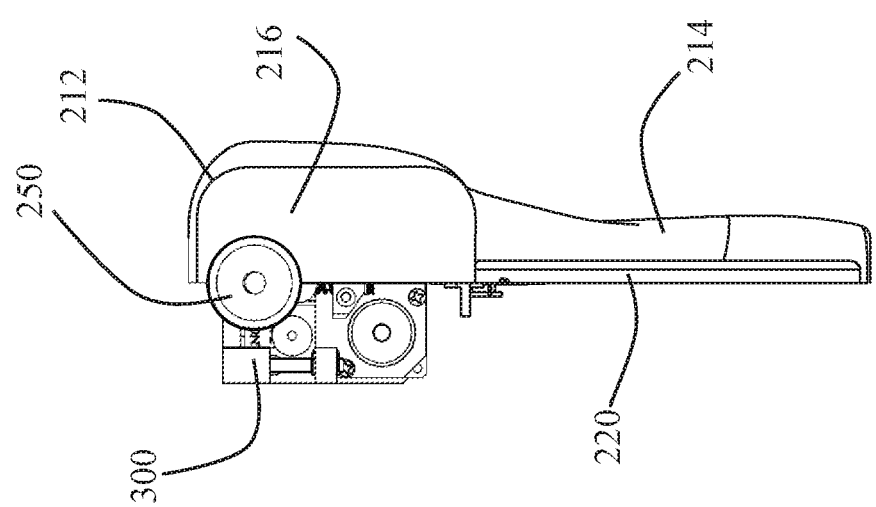
FIG. 2D is a front end view of the assemblies located within the housing in accordance with a preferred embodiment of the present invention.
Figure 3A:
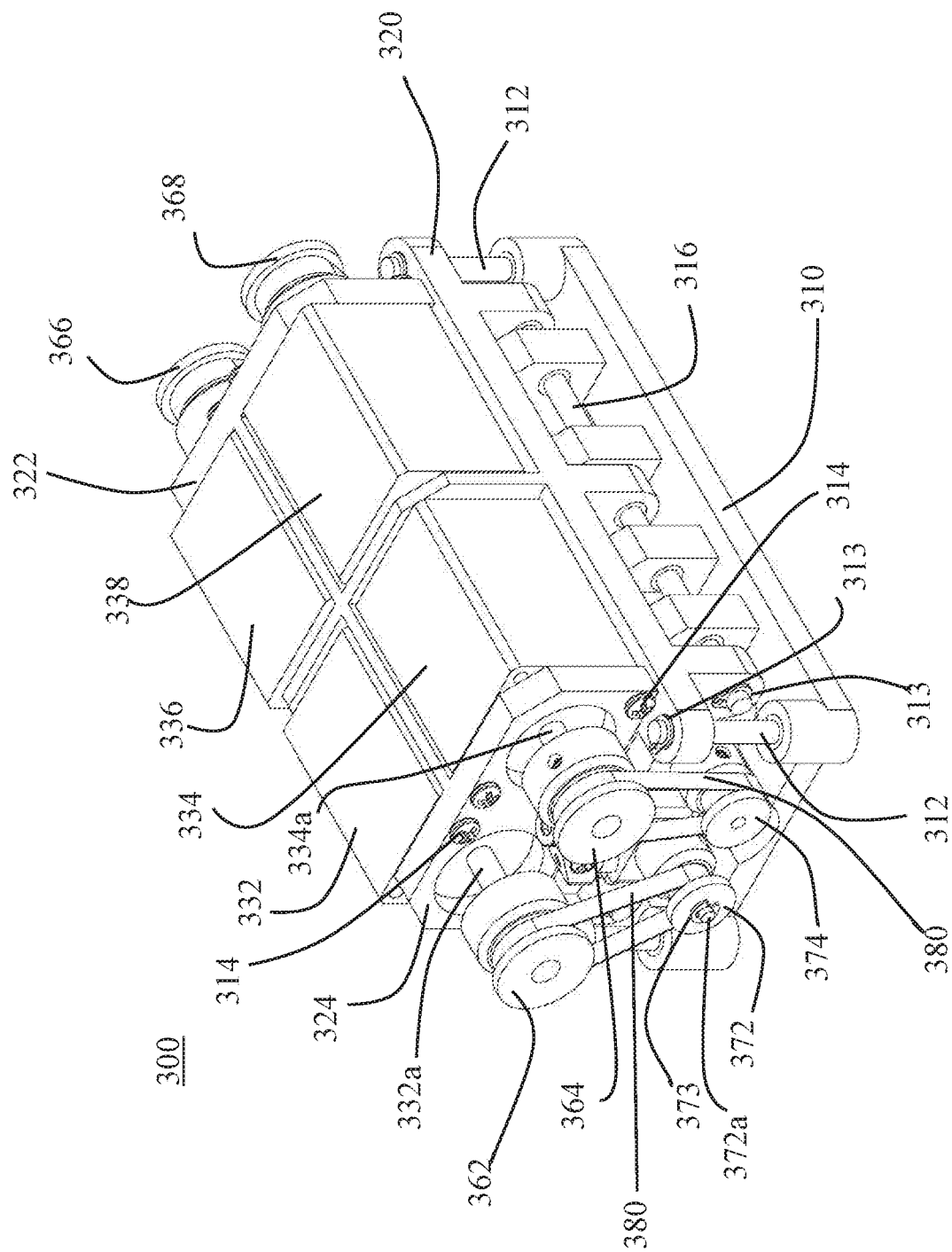
FIG. 3A is a bottom perspective view of a motor assembly of a robotic surgical system in accordance with a preferred embodiment of the present invention.
Figure 3E:
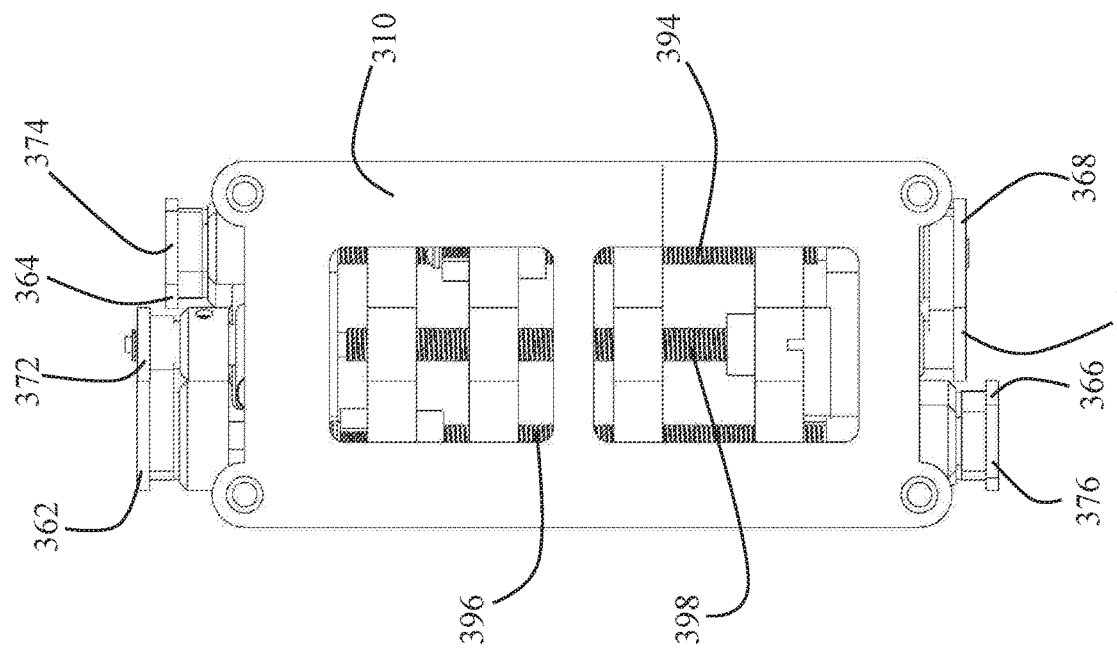
FIG. 3E is a top view of a motor assembly of a robotic surgical system in accordance with a preferred embodiment of the present invention.
Figure 3D:
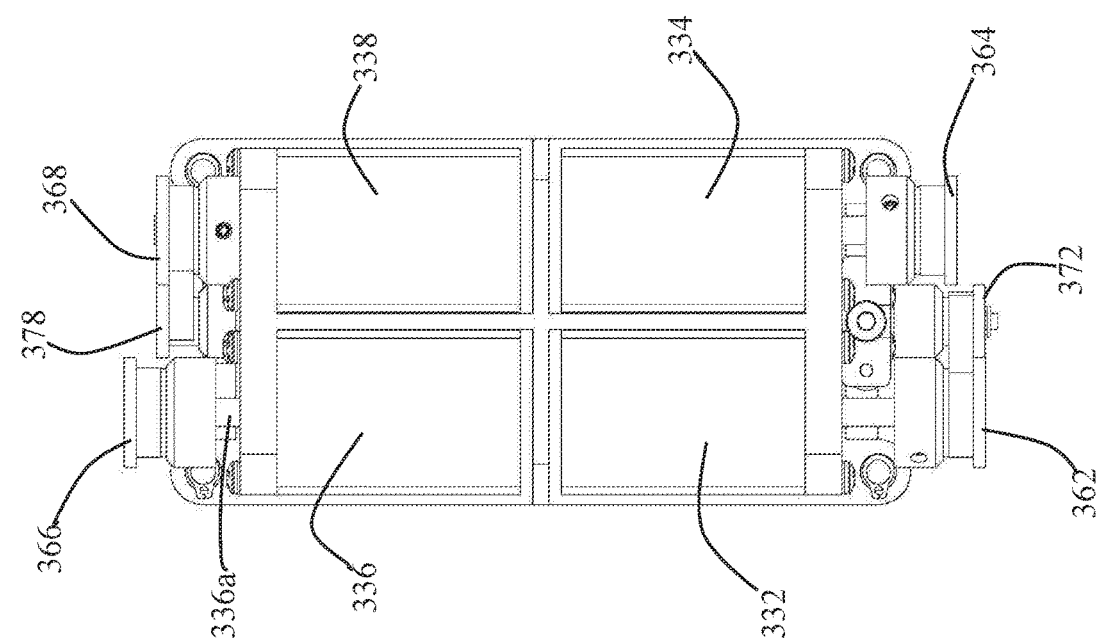
FIG. 3D is a bottom view of a motor assembly of a robotic surgical system in accordance with a preferred embodiment of the present invention.

The preferred embodiments of the inventions are described with reference to the drawings. As shown in FIGS. 1A-1I the robotic surgical system 100 of the present invention is composed primarily of three components: (1) a housing or base 200, an arm assembly 400, and a drive system or motor assembly 300 (inside the housing 200 as shown in FIG. 2B). The motor assembly 300 is positioned within the housing or base 200. The housing or base 200 preferably is reusable and provides the platform for the system. The drive system or motor assembly 300 is a single port surgical access device, which allows for insertion of the arm assembly into the single port. The arm assembly 400 may be a reusable, disposable or partially reusable/partially disposable positioning arm for supporting and positioning surgical instruments at or near the distal end of the arm.

As shown in FIGS. 2A-2E, in a preferred embodiment the housing 200 may be in the form of a hand piece 210 having a body portion 212 and a grip portion 214. The housing may be formed of a rigid materials such as ABS plastic. A manual actuator 220 is provided for manually actuating a surgical tool such as forceps, scissors, leeps, etc. attached at the distal end of the arm assembly 400. As shown in FIGS. 2A-2I, the actuator 220 may be in the form of a scissor grip, but the actuator or trigger 220 also could take any other known form. A nosecap 250, for example, made of re-enforced ABS plastic, is positioned in line with the single port in the motor assembly for receiving the proximal end of the arm assembly. The body portion 212 may have an angled front portion 216 adjacent the nosecap 250. A joystick cap 292 extends outside the housing 200 from a controller box 600 located within the housing 200. The motor assembly 300 and the controller box 600 are positioned within the housing 210. Similarly, batteries for powering the system can be within the housing 210 and/or an electrical connector for connecting to an external power source may be provided.

Within the housing 210 along with the motor assembly 300 and the controller box 600 is a pivot 224 around which the actuator 220 rotates, a translating member 226 for translating movement of the actuator 220 to the control rod in the arm assembly 200 for opening, closing or otherwise manually actuating the surgical tool at the distal end of the arm assembly 200. The translation member 226 may have a ridged or toothed edge that may engage with a pawl 228 for locking the actuator in a desired position. Further there is a release member or members 225, 227 for manually releasing the pawl 228. The actuator 220 may have an extended portion 220 with an opening for connecting to the translation member 226 to create leverage for the actuator. Further, additional linkage 229 may be used to further translate movement of the actuator 220 to the desired control rod in the arm assembly 200.

A motor assembly 300 of a preferred embodiment of the present in invention is described with reference to FIGS. 3A-3G. The motor assembly has a frame formed by a plurality of frame members 310, 320, 322, 324 connected together, for example, by rods or pins 312, 316, retainer clips 313 and screws 314. While the frame shown in the figures and described herein has multiple component parts connected together, other frame designs with fewer or more component parts of a unitary design may be used with the invention. Still further, instead of a frame the motors may be mounted in other ways in or two the housing.

The motor assembly has a plurality of electric motors 332, 334, 336, 338 secured to the frame, for example, by screws 314. Other means for securing the motors to the frame, such as bolts, pins, glue or any other means, may be used. In a preferred embodiment, the electric motors are high-torque compact micro stepper motors. While four electric motors are shown and described herein, other numbers of motors may be used. Each motor 332, 334, 336, 338 has a drive shaft 332a, 334a, 336a, 338a extending therefrom. The motors 332, 334, 336, 338 are arranged in a 2×2 matrix in a plane with two of the motors 332, 334 having their drive shafts 332a, 334a extending in a first direction and the other two motors 336, 338 having their drive shafts 336a, 338a extending in a second direction opposite the first direction. A pulley 362, 364, 366, 368 having a groove for receiving a drive band is connected to each drive shaft 332a, 334a, 336a, 338a of each motor 332, 334, 336, 338.

Each pulley 362, 364, 366, 368 is connected to a secondary pulley 372, 374, 376, 378 by a drive band 380. Secondary pulleys 374, 376, 378 each are connected to a drive screw 394, 396, 398, which are mounted in the fame by a rods 374a, 376a, 378a. Secondary pulley 372 is connected to a friction drive 372a. The secondary pulleys are secured to the friction drive or rods, for example, by retainer clips 373.

Figure 4A:
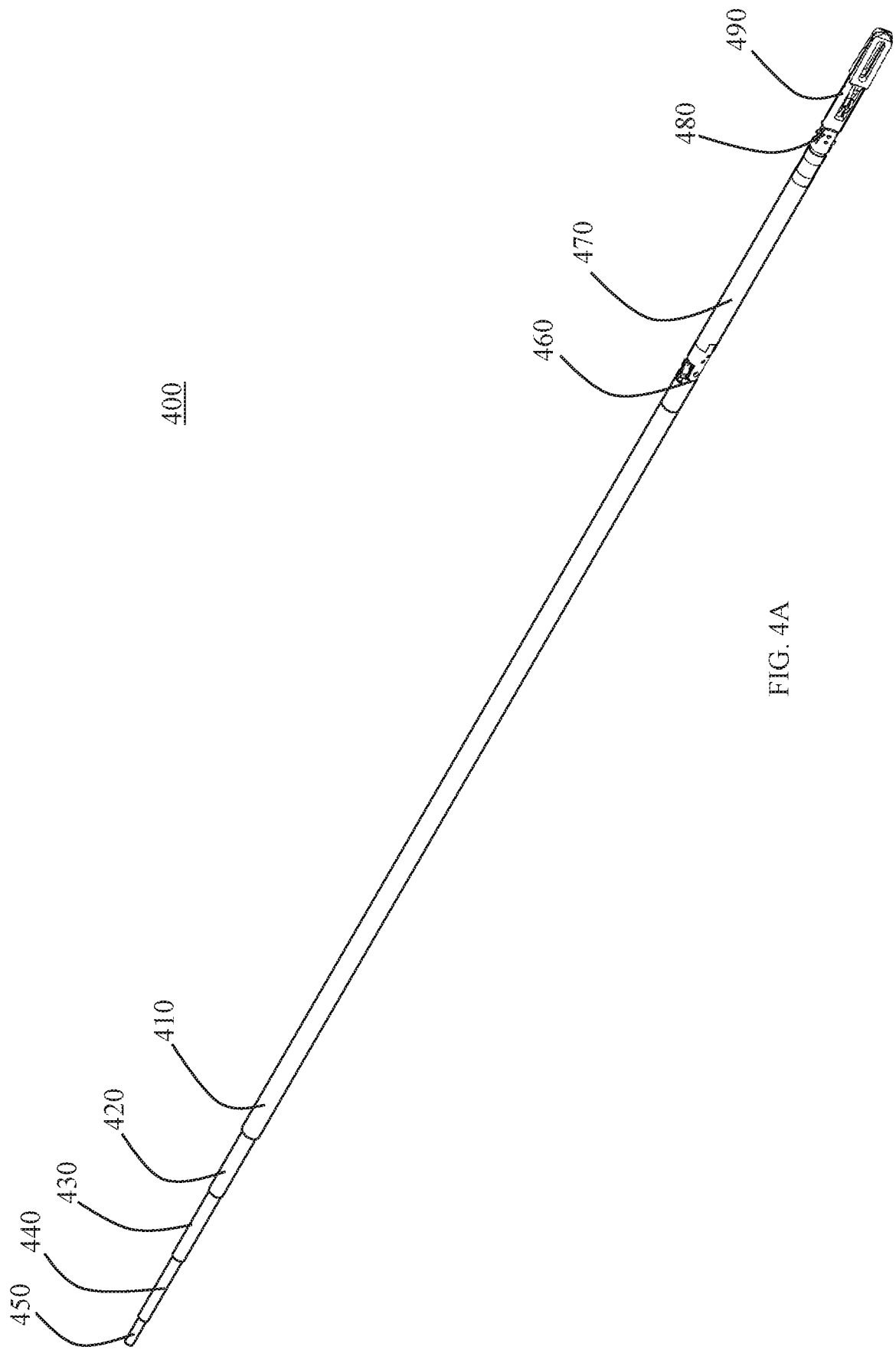
FIG. 4A is a perspective view of an arm assembly of a robotic surgical system in accordance with a preferred embodiment of the present invention.
Figure 4B:
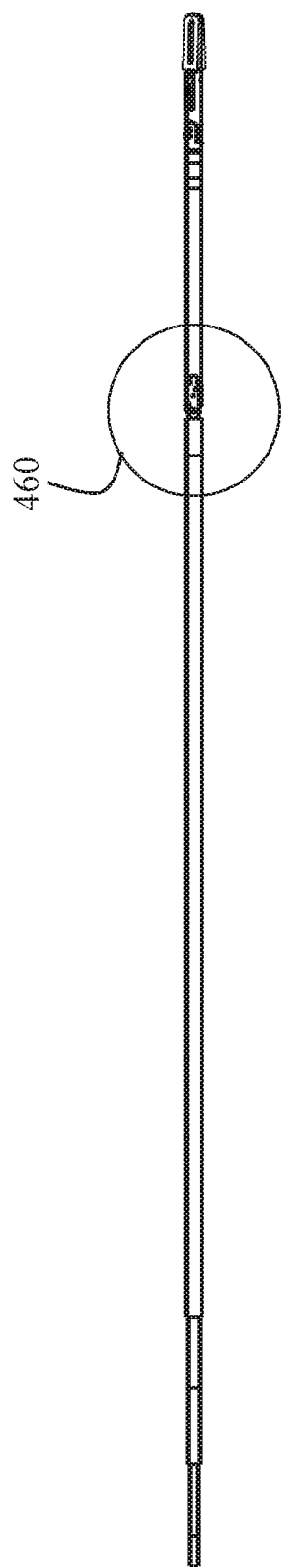
FIG. 4B is a first side view of an arm assembly illustrating a first degree of freedom of a robotic surgical system in accordance with a preferred embodiment of the present invention.
Figure 4C:
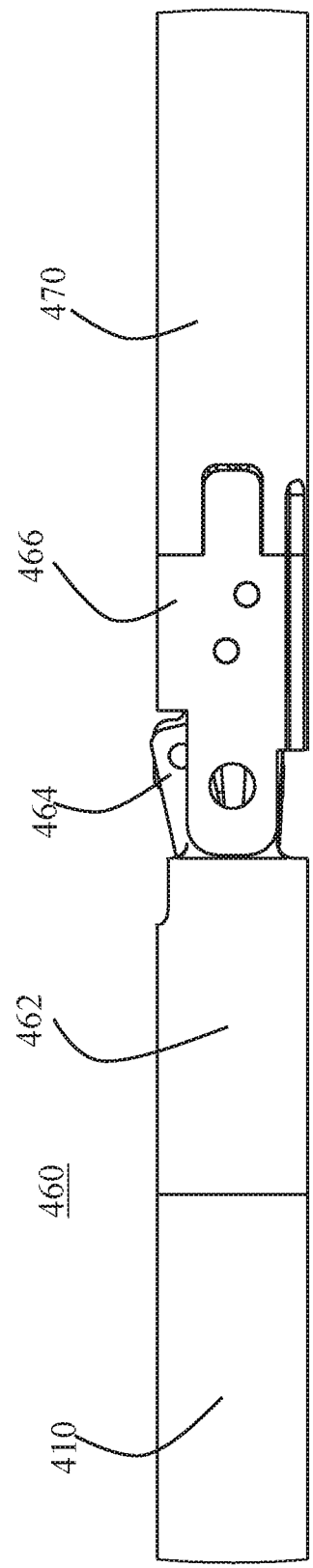
FIG. 4C is an enlarged first side view of the first degree of freedom of an arm assembly of a robotic surgical system in accordance with a preferred embodiment of the present invention as shown in FIG. 4B.
Figure 4F:
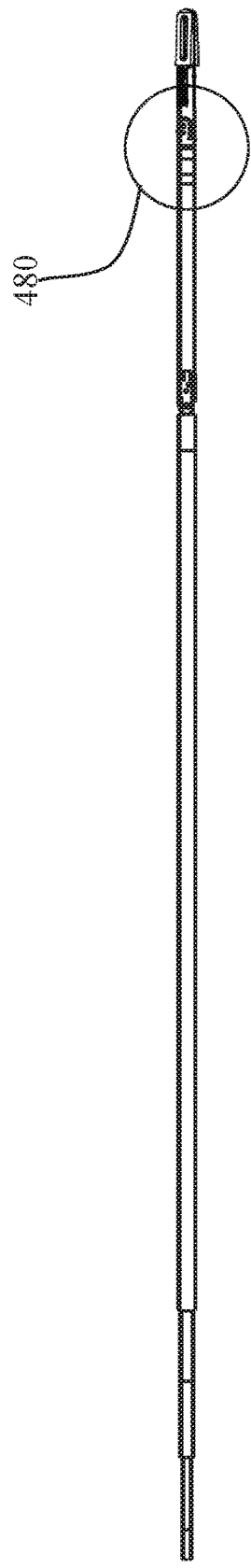
FIG. 4F is first side view of an arm assembly illustrating a second degree of freedom of a robotic surgical system in accordance with a preferred embodiment of the present invention.
Figure 4G:
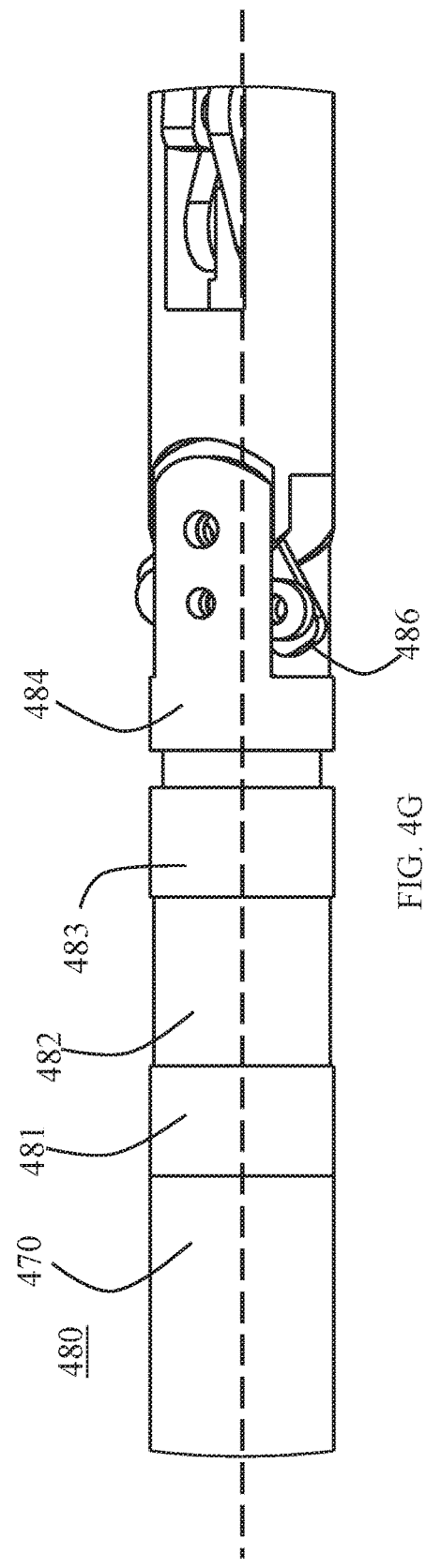
FIG. 4G is a first side view of the second degree of freedom of an arm assembly of a robotic surgical system in accordance with a preferred embodiment of the present invention as shown in FIG. 4F.
Figure 4H:
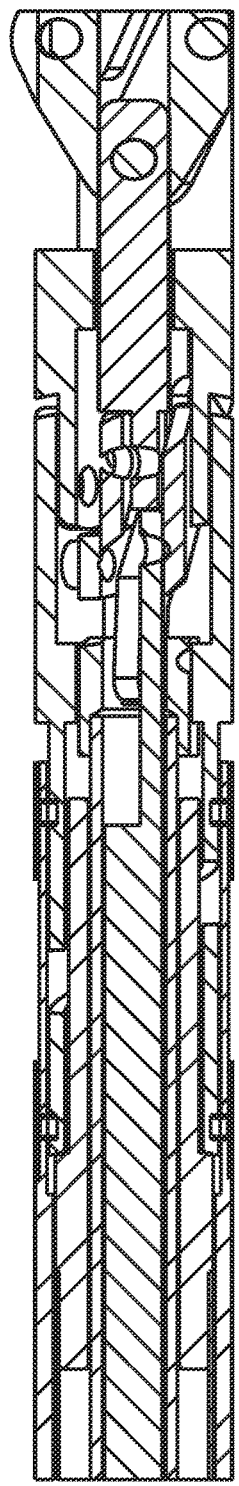
FIG. 4H is a first cross-section view of a second degree of freedom of an arm assembly of a robotic surgical system in accordance with a preferred embodiment of the present invention as shown in FIG. 4F.

The arm assembly 400 of a preferred embodiment is described with reference to FIGS. 1I and 4A-4N. As shown in FIG. 1I the arm assembly 400 has four degrees of freedom DOF1, DOF2, DOF3, DOF4 controlled by the motors 332, 334, 336, 338 and one degree of freedom DOF5 controlled by the actuator 220. The arm assembly 400 has a plurality of nested control rods or actuation tubes 410, 420, 430, 440, 450 for controlling various degrees of freedom of the arm assembly. Control rod 410, also referred to as the long arm, controls the first degree of freedom DOF1, which is 0-360° rotation of the entire arm assembly. Control rod 420 controls the second degree of freedom DOF2, which is a 0-45° bending movement at joint 460. Control rod 430 controls the third degree of freedom DOF3, which is a 0-180° rotation of the distal arm 470. Control rod 420 controls the fourth degree of freedom DOF4, which is a 0-45° bending movement at joint 480. Control rod 410 controls the movement, such as opening and closing, of a surgical tool 490 at the distal end of the arm assembly. The first four degrees of freedom DOF1-DOF4 are controlled by the motors 332, 334, 336, 338 and the fifth degree of freedom DOF5 is controlled by the actuator 220.

The joint 460 provides for the second degree of freedom DOF2 and is shown in greater detail in FIGS. 4B-4E. The long arm 410 is connected to joint member 462. Joint member 466 is connected to joint member 462 in a hinged arrangement and to distal arm 470. Linkage 464 is connected to control arm 420 and provides for limited movement between hinge members 462, 466.

The joint 480 provides the third degree of freedom DOF3 and is shown in greater detail in FIGS. 4F-4K. Distal arm 470 is connected to members 481, 482, 483. Hinge member 484 is connected to a control rod that provides for the fourth degree of freedom DOF4, which is accomplished by rotating the hinge member 484. The rotation of hinge member 484 rotates surgical tool 490 at the distal end of the arm assembly. The surgical tool 490 is connected to hinge member 484 and linkage 486, which is connected to a control arm to produce a bending movement between hinge member 484 and surgical tool 490. An exemplary surgical tool 490 is shown in FIGS. 4L-4N.

Figure 5A:
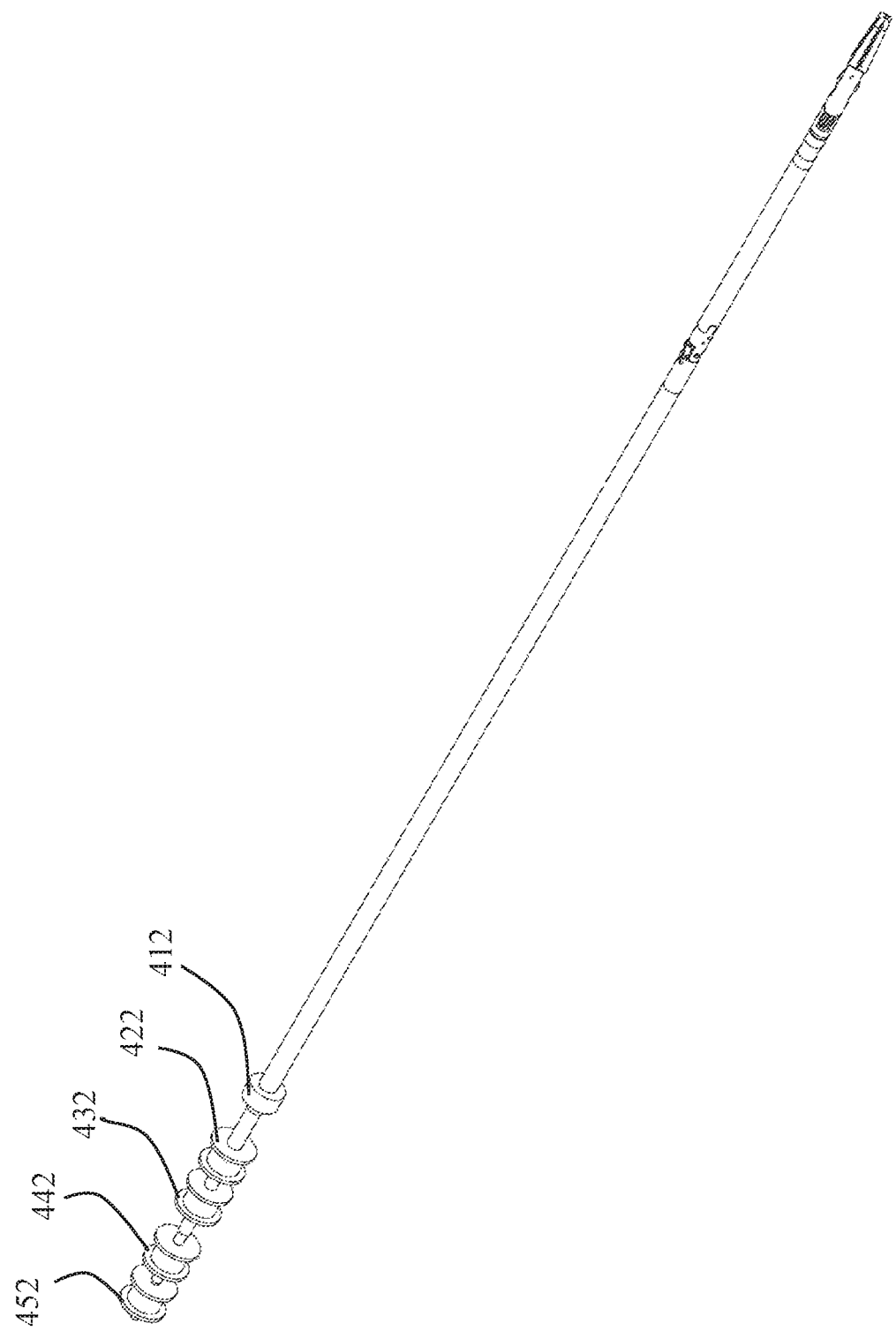
FIG. 5A is a perspective view of an arm assembly of a preferred embodiment of the present invention prior to connection to a motor assembly of a preferred embodiment of the present invention.
Figure 5B:
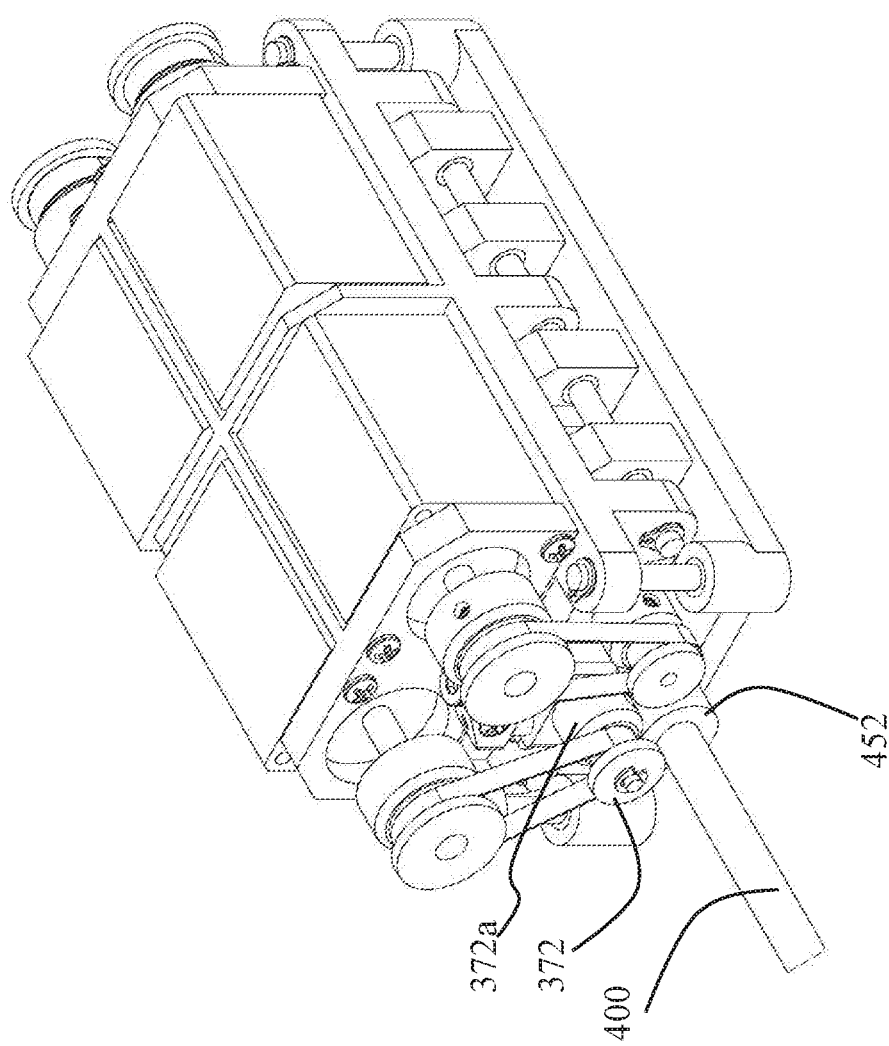
FIG. 5B is a bottom perspective view of a motor assembly with an arm assembly in accordance with a preferred embodiment of the present invention.
Figure 5E:
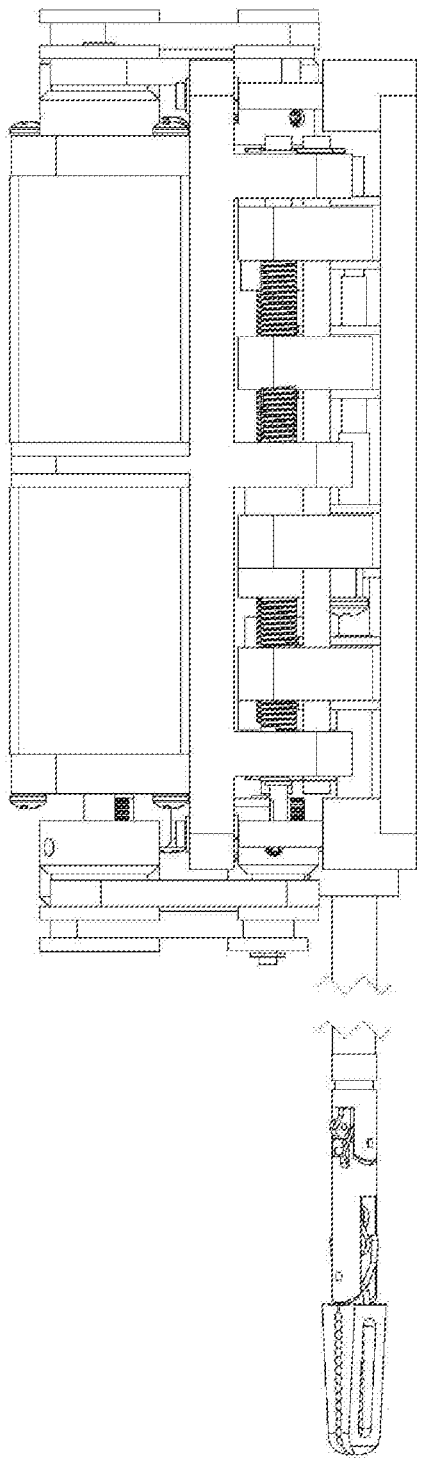
FIG. 5E is a second side view of a motor assembly with an arm assembly in accordance with a preferred embodiment of the present invention.
Figure 5F:
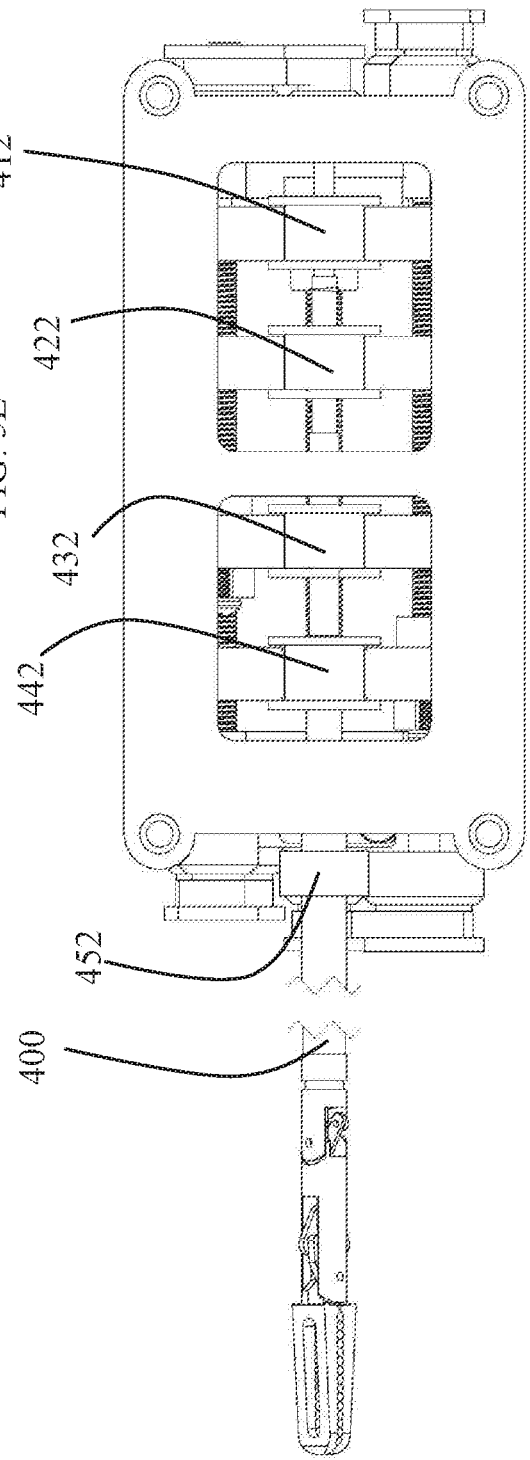
FIG. 5F is a top view of a motor assembly with an arm assembly in accordance with a preferred embodiment of the present invention.

As shown in FIG. 5A, when assembled with the motor assembly, a plurality of spools 412, 422, 432, 442 are connected to the control rods 410, 420, 430, 440. A friction drive or member 452 is connected to control rod 450. The proximal portion of the arm assembly is inserted into channel 369 of the motor assembly 300. Once inserted the friction member 452 engages with friction drive 372a. Spools 422, 432, 442 are connected to drive screws 392, 394, 396. Spool 412 is connected to the actuator 220 and associated structures.

Figure 6:
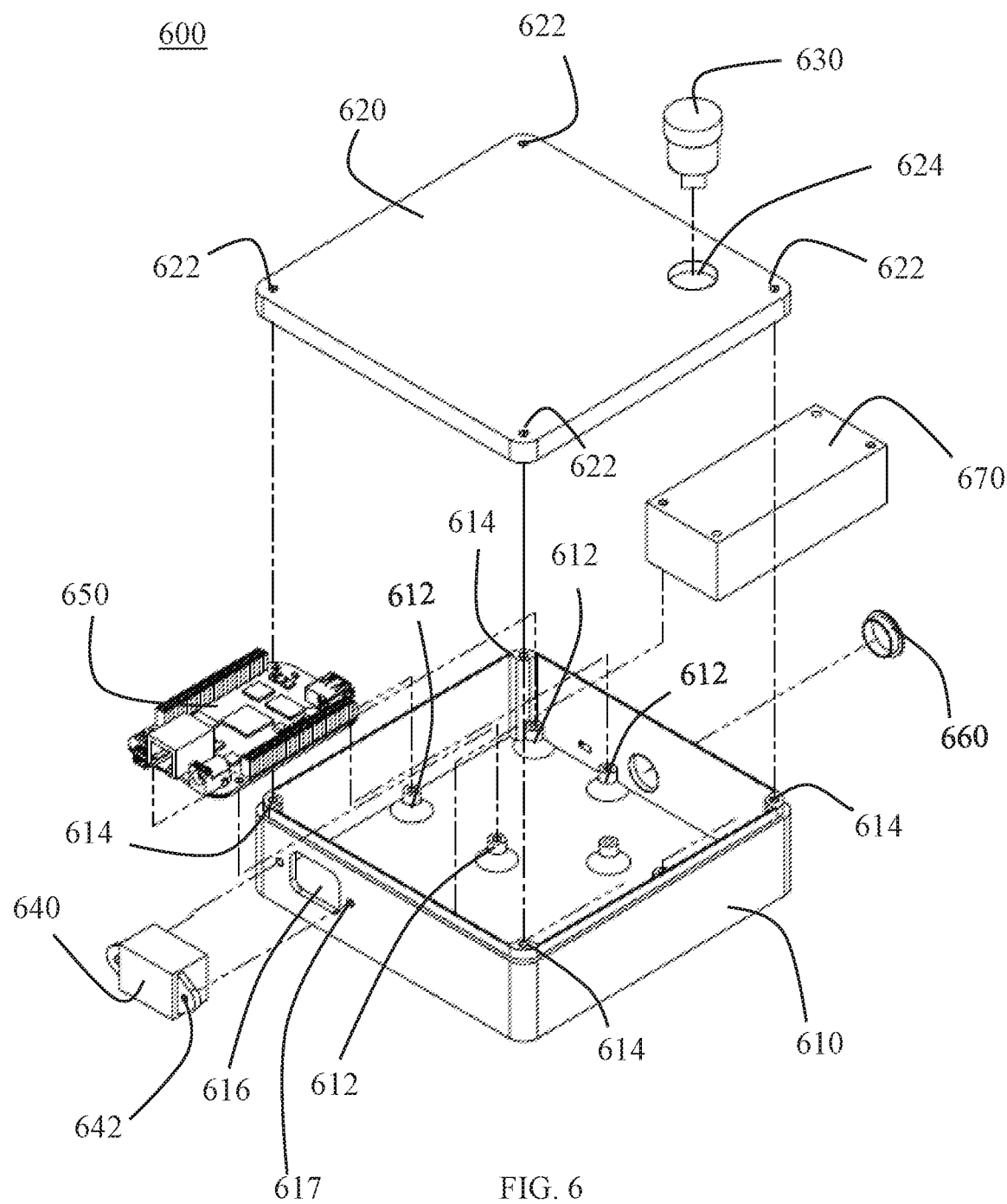
FIG. 6 is an assembly diagram of a control box assembly in accordance with a preferred embodiment of the present invention.

The system has a control box assembly such as is shown in FIG. 6. The control box assembly 600 has a box chassis 610 and lid 620. The box chassis 610 has means for securing the lid 620 to the box 610, such as threaded holes or the like 614. The lid 620 has holes 622 for receiving screws or other connector members (not shown) for securing the lid 620 to the box chassis 610. The box chassis 610 has an opening 616 on one side for receiving an input power jack 640, which may, for example, the connected to the box chassis 610 by screws extending through holes 642 into threaded holes 617 in the box chassis. The box chassis 610 has another opening for receiving a robot connector 660. The box chassis 610 has within it a power converter 670 and a backplane or PCB board 650 held in the box chassis on support members 612. The lid 620 has a hole 624 for receiving an illuminated power switch 630. The input power jack is connected to the backplane, which is connected to the converter box. The converter box converts the input power from an electrosurgical generator, wall outlet, or other power source, and outputs converted power through robot connector 660 to the hand piece of the robotic surgical instrument.

Figure 7A:
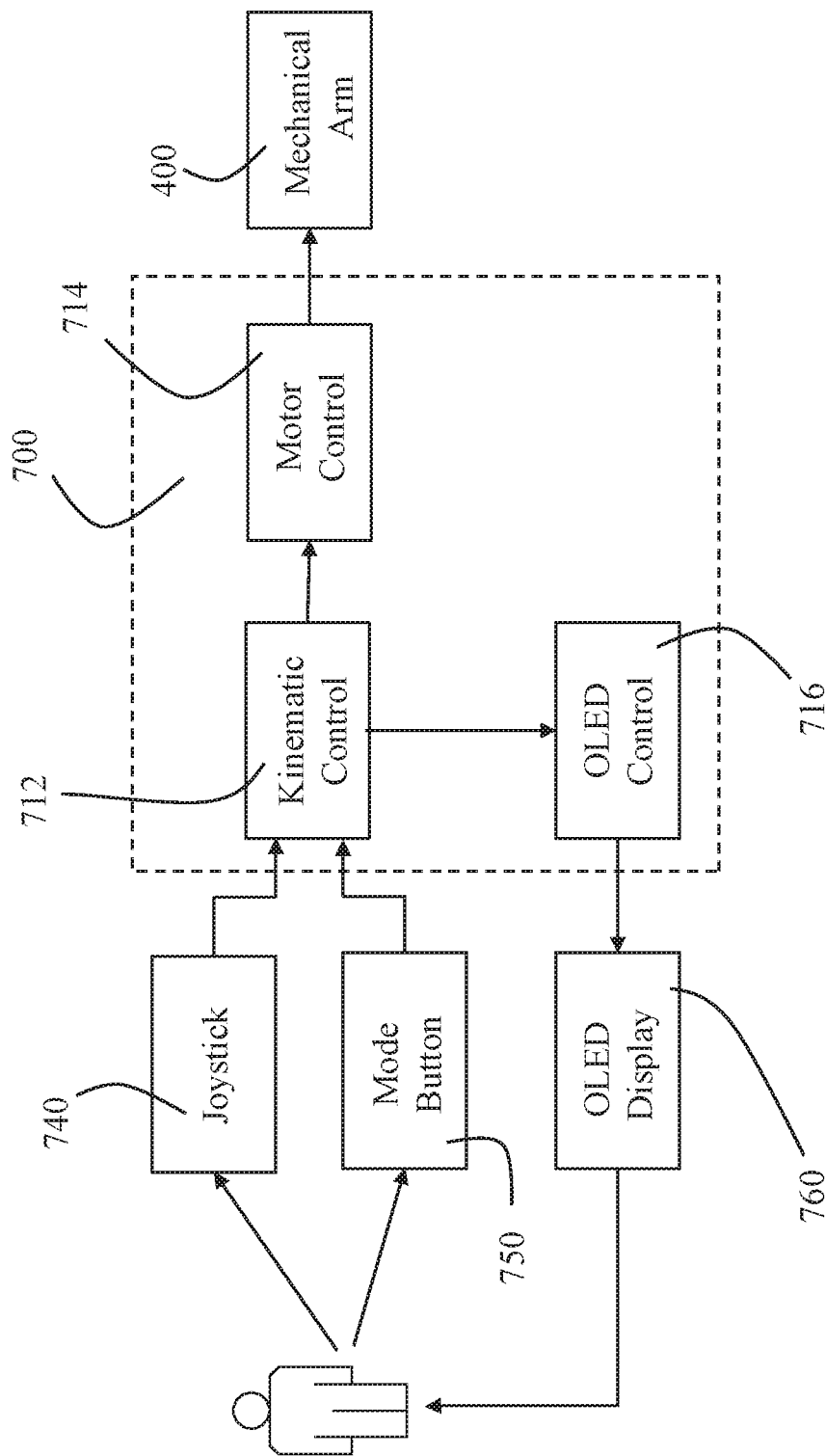
FIG. 7A is a block diagram of a high level architecture of a system in accordance with a preferred embodiment of the present invention.

An exemplary control workflow is shown in FIG. 7A. A surgeon controls the robotic surgical system through controls on the hand piece. The controls include a joystick 740 and a mode button or buttons 750. The surgeon may view operational status messages and/or settings on an OLED display 760 (described in connection with the alternative embodiment discussed below). The control system 700 provides kinematic control 712 and motor control 714 for controlling the mechanical arm 400 and OLED control 716 for controlling the OLED display 760.

Figure 7B:
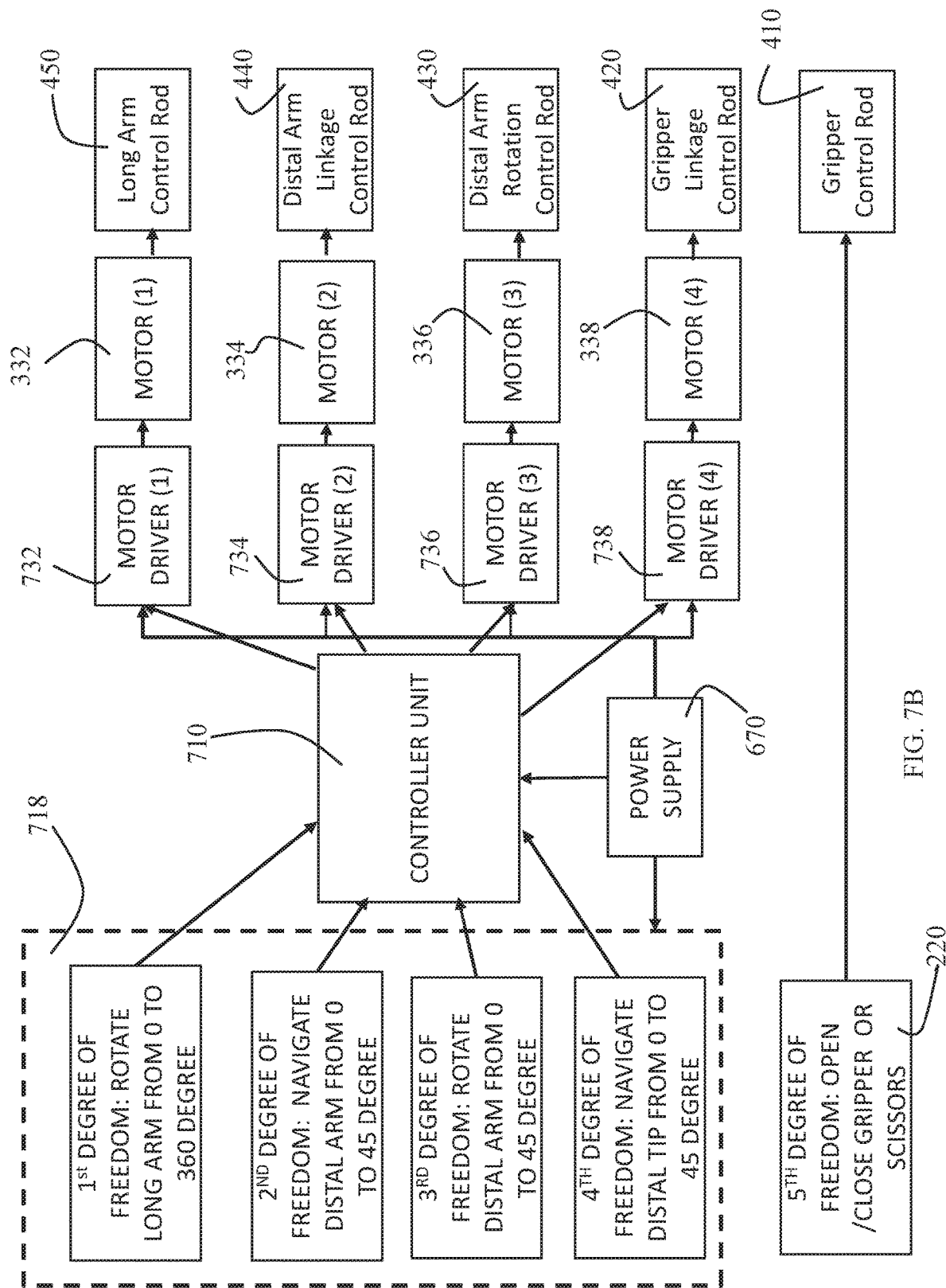
FIG. 7B is a block diagram illustrating an architecture of a robotic surgical system in accordance with a preferred embodiment of the present invention.

An exemplary control architecture is shown in FIG. 7B. Four degrees of freedom DOF1, DOF2, DOF3, DOF4 (718) are controlled via the joystick 290 in a hand piece. A controller unit 710 in the hand piece sends control signals via motor drivers 732, 734, 736, 738 to operate the four electric motors 332, 334, 336, 338. Power supply 670 may be batteries within the housing 210 or may be provided from an external source such as controller box 600 via an electrical connector in the housing. The power supply powers the motors, controller unit and joystick controller box 600. While a joystick controller 290 is described with respect to the preferred embodiments, other controls structures such as switches or dials also may be used with the invention.

Figure 7C:
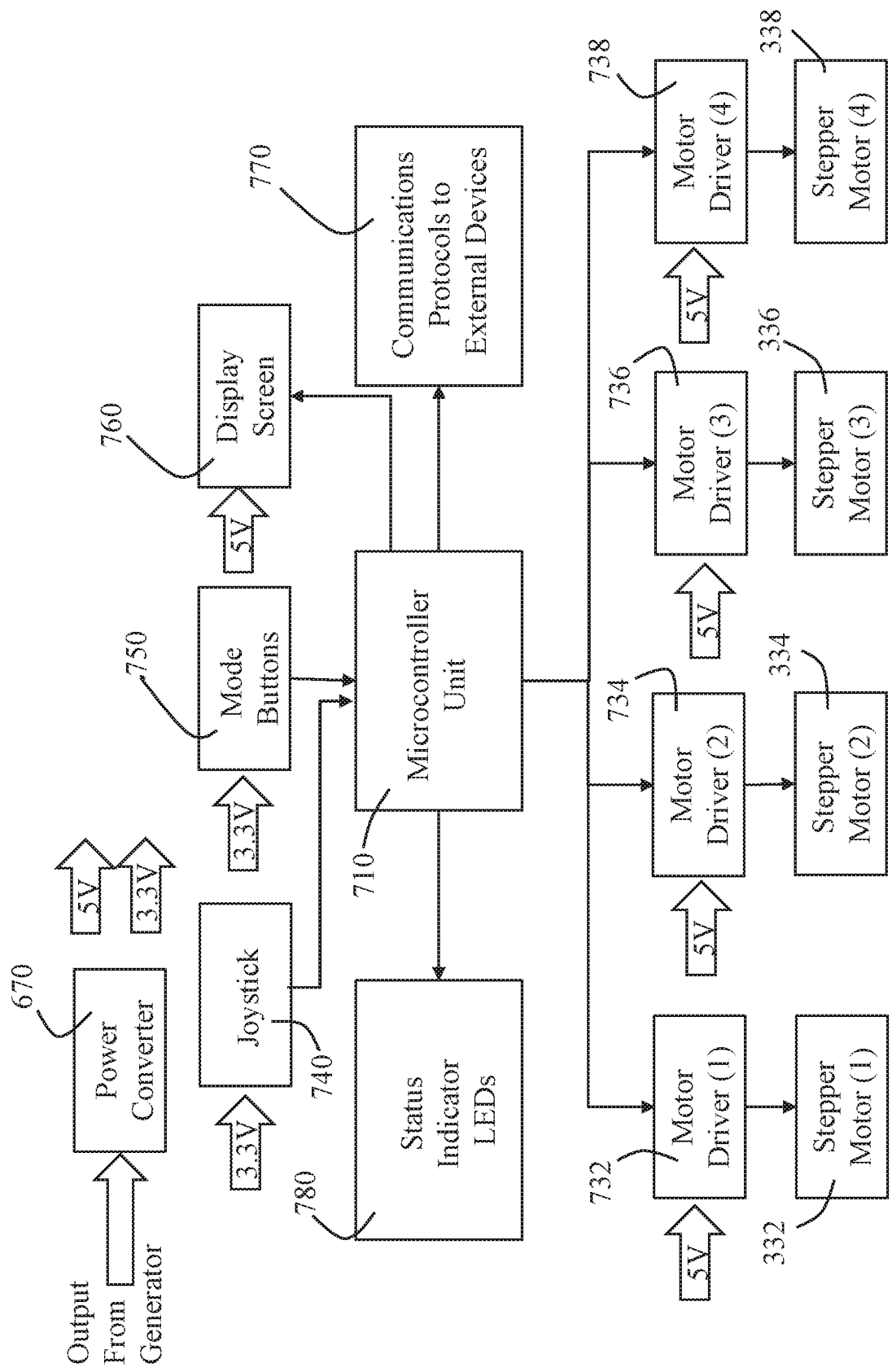
FIG. 7C is a flow diagram for a control board in accordance with a preferred embodiment of the present invention.

FIG. 7C is a flow diagram illustrating the work flow of the control board in a robotic surgical system in accordance with the present invention. The power converter 670 in the control box 600 receives electrical energy from an output of an electrosurgical generator (not shown). The power converter 670 outputs 5V and 3.3V DC power to the robotic surgical hand piece through cords (not shown) connecting the hand piece to the control box 600. The control box 600 similarly is connected to the electrosurgical generator through an electrical cord or cords (not shown). The 3.3 V power received by the hand piece from the power converter 670 is used to power the joystick 740 and the mode button(s) 750. The 5V power received by the hand piece from the control box 600 is used to power the motors and motor drivers along with a display screen 760. A microcontroller unit 710 is powered by power received from the power converter 670, received inputs from the mode button(s) 750 and joystick 740 and controls the motor drivers and motors, one or more status indicator LED's 780 and communications to external devices 770.

Figure 8A:
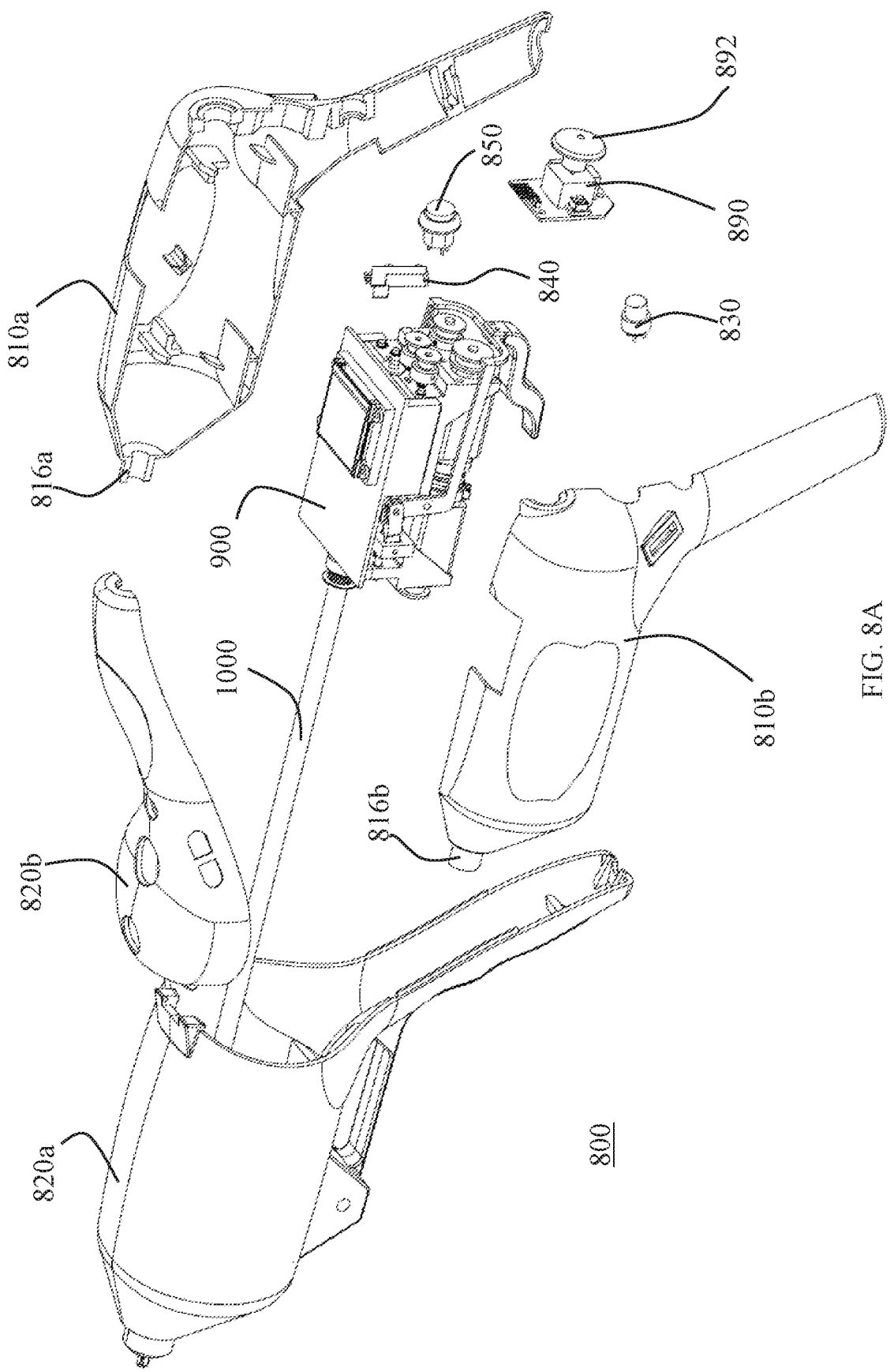
FIG. 8A is an assembly drawing of a robotic surgical system in accordance with an alternative preferred embodiment of the present invention.
Figure 8B:
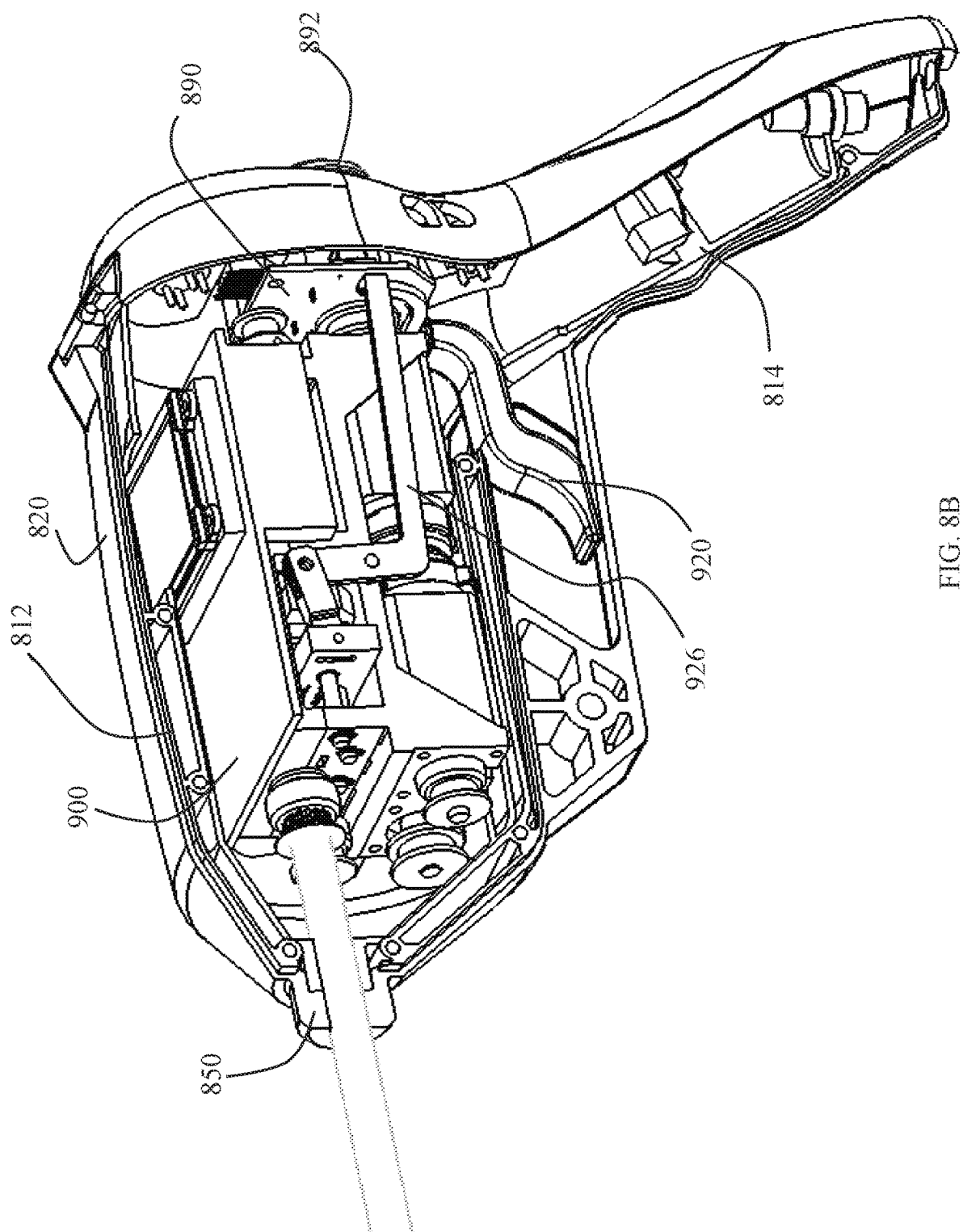
FIG. 8B is a side perspective view of the interior of a hand piece of a robotic surgical system in accordance with an alternative preferred embodiment of the present invention.
Figure 8C:
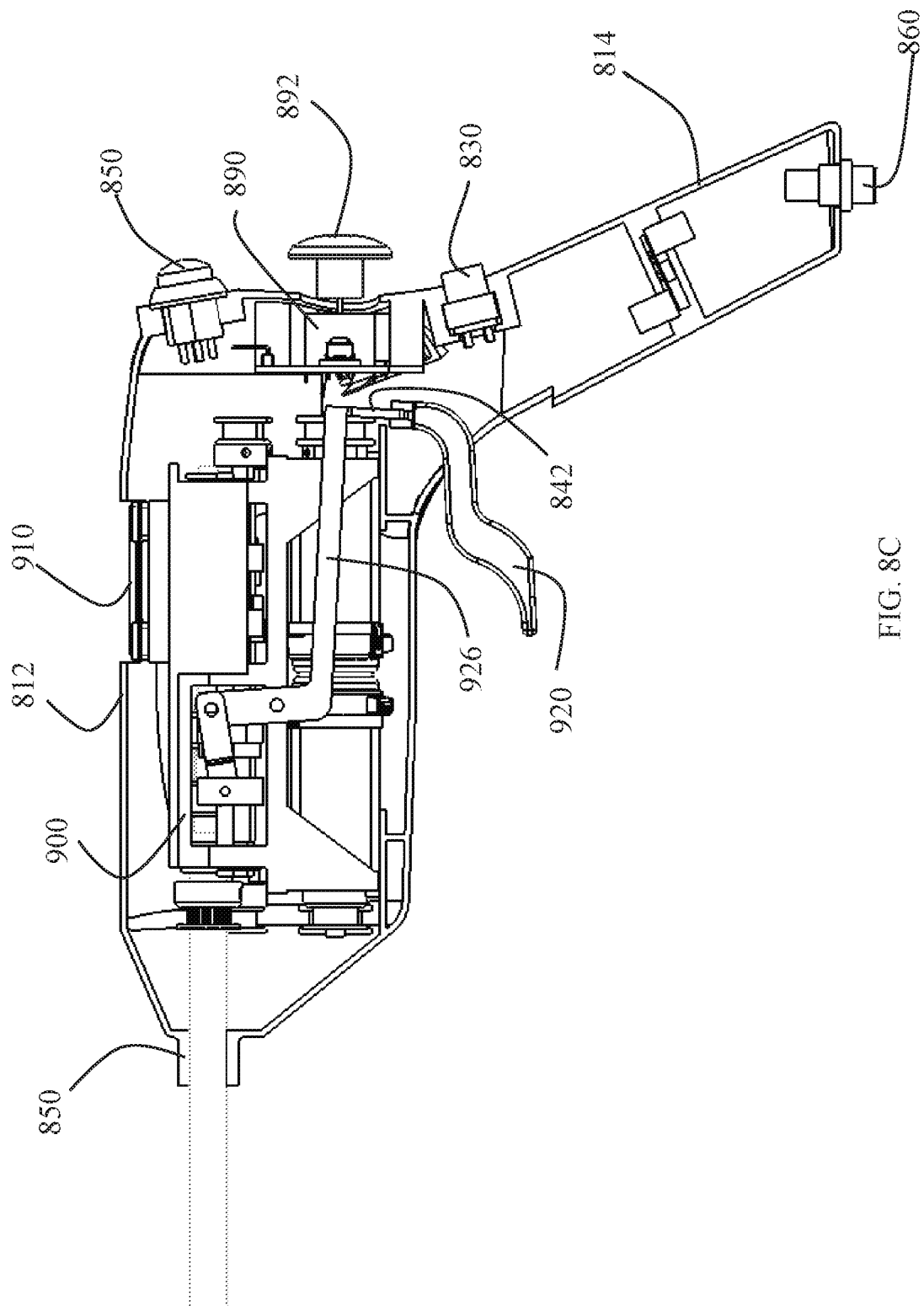
FIG. 8C is a side view of the interior of a hand piece of a robotic surgical system in accordance with an alternative preferred embodiment of the present invention.
Figure 8D:
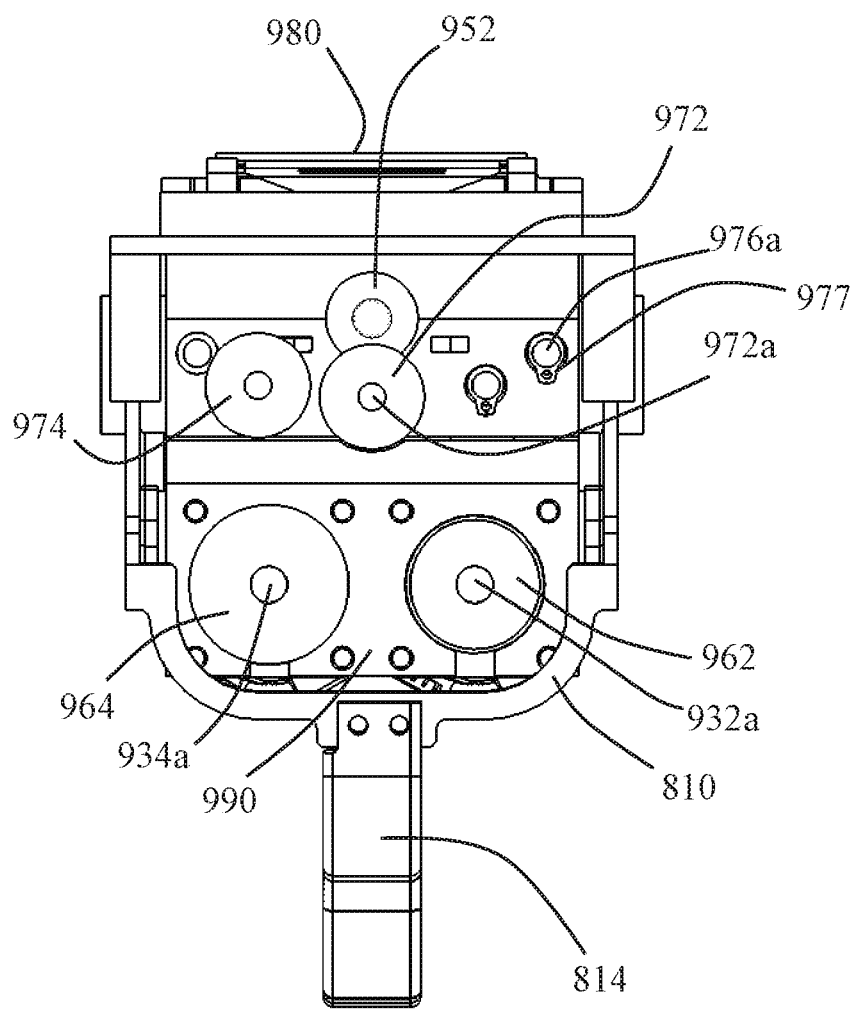
FIG. 8D is a front view of the interior of a hand piece of a robotic surgical system in accordance with an alternative preferred embodiment of the present invention.

An alternative embodiment of a hand piece housing or casing for a robotic surgical system in accordance with the present invention is described with reference to FIGS. 8A-8D. The terms "housing," "shell," "case" and "casing" all are used interchangeably in this description. The hand piece has a rigid inner case 810 that is formed or two pieces 810a and 810b that can be snapped, connected or otherwise secured to one another to encase a motor assembly 900 and house various elements such as a mode button 830, a locking button 840, a power button 850 and a joystick 890. The inner case 810 has a plurality of openings through which elements such as mode button 830, locking button 840, power button 850 and joystick 890 protrude and can be accessed and operated by a user. The joystick 890 may have a cap 892. Other buttons or controls also may have elements such as caps or coatings. The inner housing 810 further has an opening or window for accommodating a screen, which in FIGS. 8A-8 is shown attached to the motor assembly 900. It will be understood that in other embodiments the screen may be mounted in the inner case 810 separately from the motor assembly 900 and be connected to the controller in the motor assembly (or elsewhere in the hand piece) with wires. The inner case 810 further has a nose cap 816 with an opening for receiving a robot arm 1000. In FIG. 8A each side 816a, 816b is form as an integral part of its respect side 810a, 810b of the case. Alternative embodiments could have a nose cap that is not integral with the inner case 810. The hand piece further has an outer case 820 having a front body portion 820a and a back portion 820b. The front body portion 820a has a nose having an opening for receiving a robot arm 1000. The back portion 820 opens or can be detached from the front body portion 820a to allow for the inner case 910 (along with everything in the inner case 810) to be inserted into the outer case front portion 820a and then the back portion 820b can be closed or attached to the front portion to enclose the inner case. The outer case 820 may be clear so the display in the motor package can be seen through the outer case 820 or may have a clear portion or may have an opening or window through which the screen can be viewed. The outer case 820 further has a plurality of openings corresponding to the openings in the inner case 810 for the under controls and LED's. The hand piece further has a connector 860 adjacent an opening in the bottom of the grip portion 814 of the inner casing 810 for receiving a power connector from control box 600 to supply power to the hand piece. The connector 860 is connected to the motor assembly in the body portion 812 of the inner case 810 by a wire/cable or wires/cables (not shown) inside the inner casing 810. The hand piece further has a trigger 920 connected to the motor assembly through a link or links 842 and extending outside both the inner case 810 and the outer case 820.

Figure 9A:
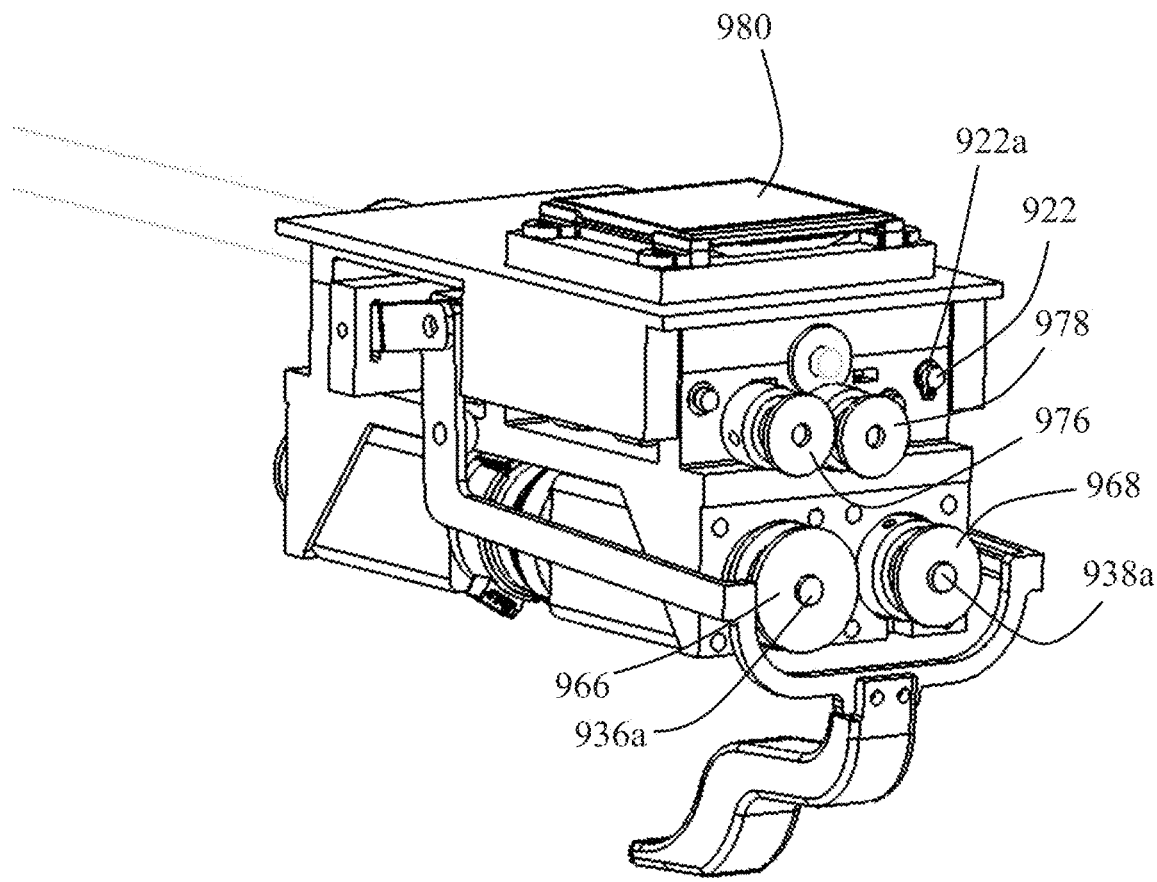
FIG. 9A is a rear perspective view of a motor assembly in accordance with an alternative preferred embodiment of the present invention.
Figure 9B:
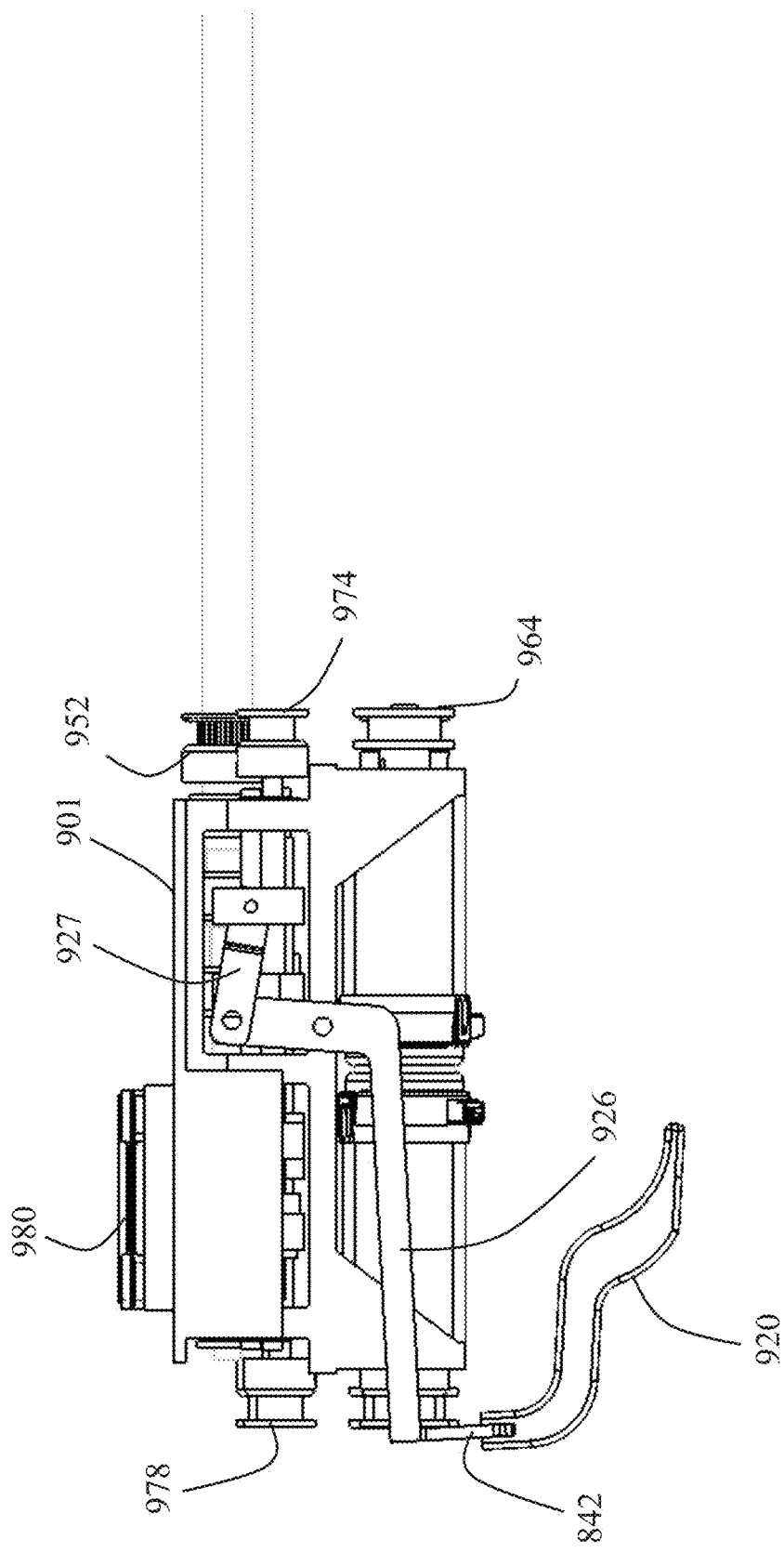
FIG. 9B is a side view of a motor assembly in accordance with an alternative preferred embodiment of the present invention.
Figure 9C:
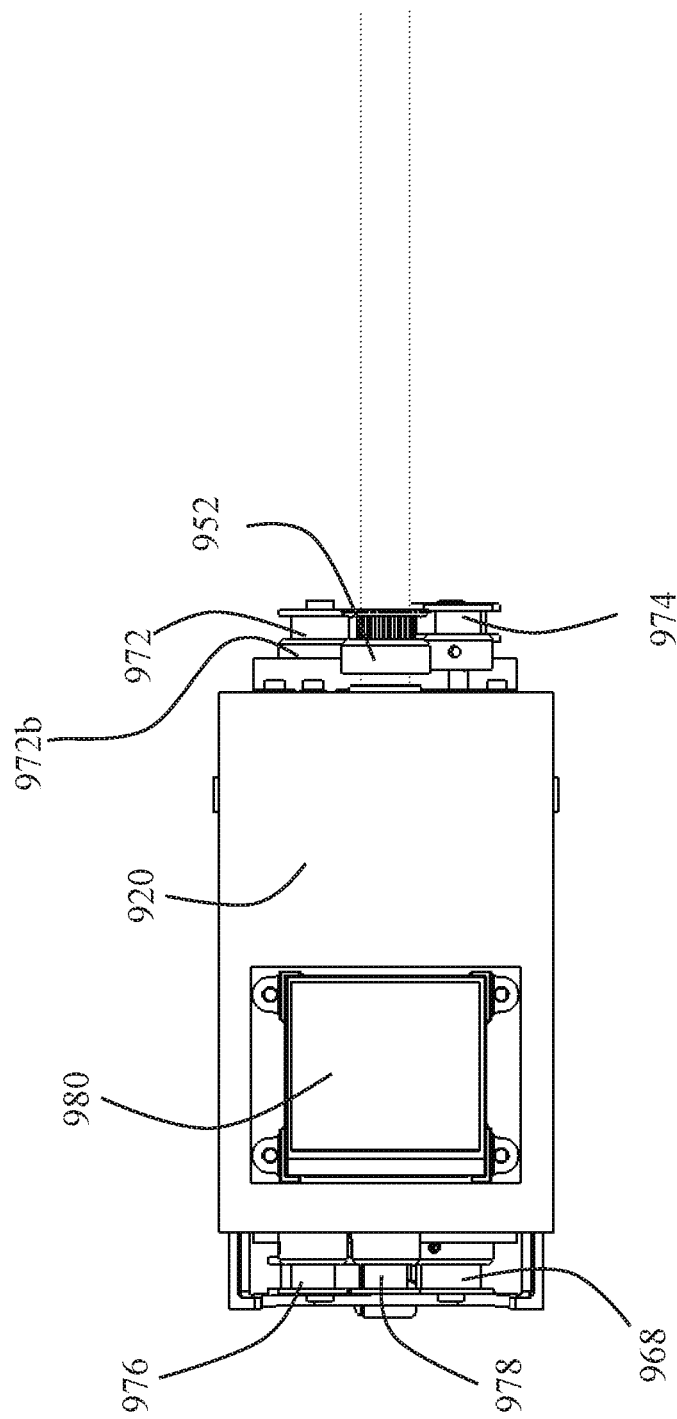
FIG. 9C is a top view of a motor assembly in accordance with an alternative preferred embodiment of the present invention.
Figure 9D:
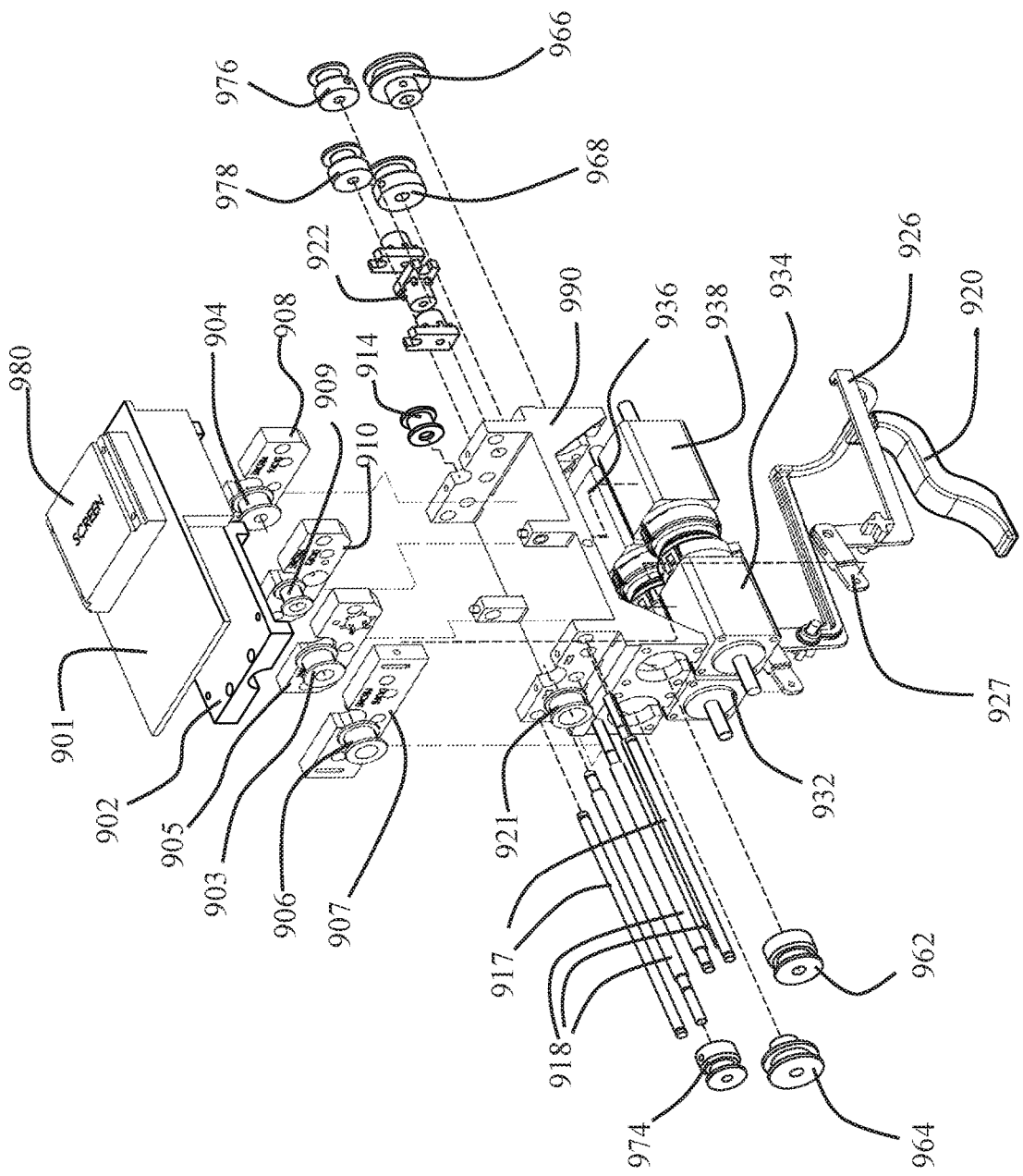
FIG. 9D is an assembly view of a motor assembly in accordance with an alternative preferred embodiment of the present invention.

The various parts in the motor assembly or package 900 are supported by the frame 990, as shown in FIG. 9A. The frame 990 has a groove near each end for receiving a mechanical arm. A plurality of slider members 905, 907, 908, 910 are mounted to the frame with slider bars 917, 918 that are secured to the frame 990 with screw nuts 922, 922a. Each slider member has a groove for receiving a mechanical arm. Four stepper motors 932, 934, 936, 938, each having a drive shaft 932a, 934a, 936a, 938a, are mounted to the frame, for example, using screws. A slider or drive ring 903, 904, 906, 909 is placed adjacent each slider member 905, 907, 908, 910 for receiving a mechanical arm. A support ring 914, 921 is placed adjacent the groove near each end of the frame 990 and a friction drive ring 952 is placed on the accessory 1000 near the front end of the frame. A cover 902 is placed on and secured to the frame 990, for example, with screws. A PCB board 901 having the system control electronics is placed on the cover 901 and a screen 980 is electrically connected to the PCB board 901 and is physically attached to the PCB board 901. A plurality of spools or pulleys 962, 964, 966, 968 are attached to the respective motor drive shafts 932a, 934a, 936a, 938a for receiving belts that drive spools or pulleys 972, 974, 976, 978 that are mounted on drive rods or shafts 917, 918 and which move actuator tubes in the mechanical arm. The motor assembly 900 further has a trigger 920, a connecting arm 926, and linkage 927 for manual activation of the tool at the distal end of the mechanical arm.

Figure 10A:
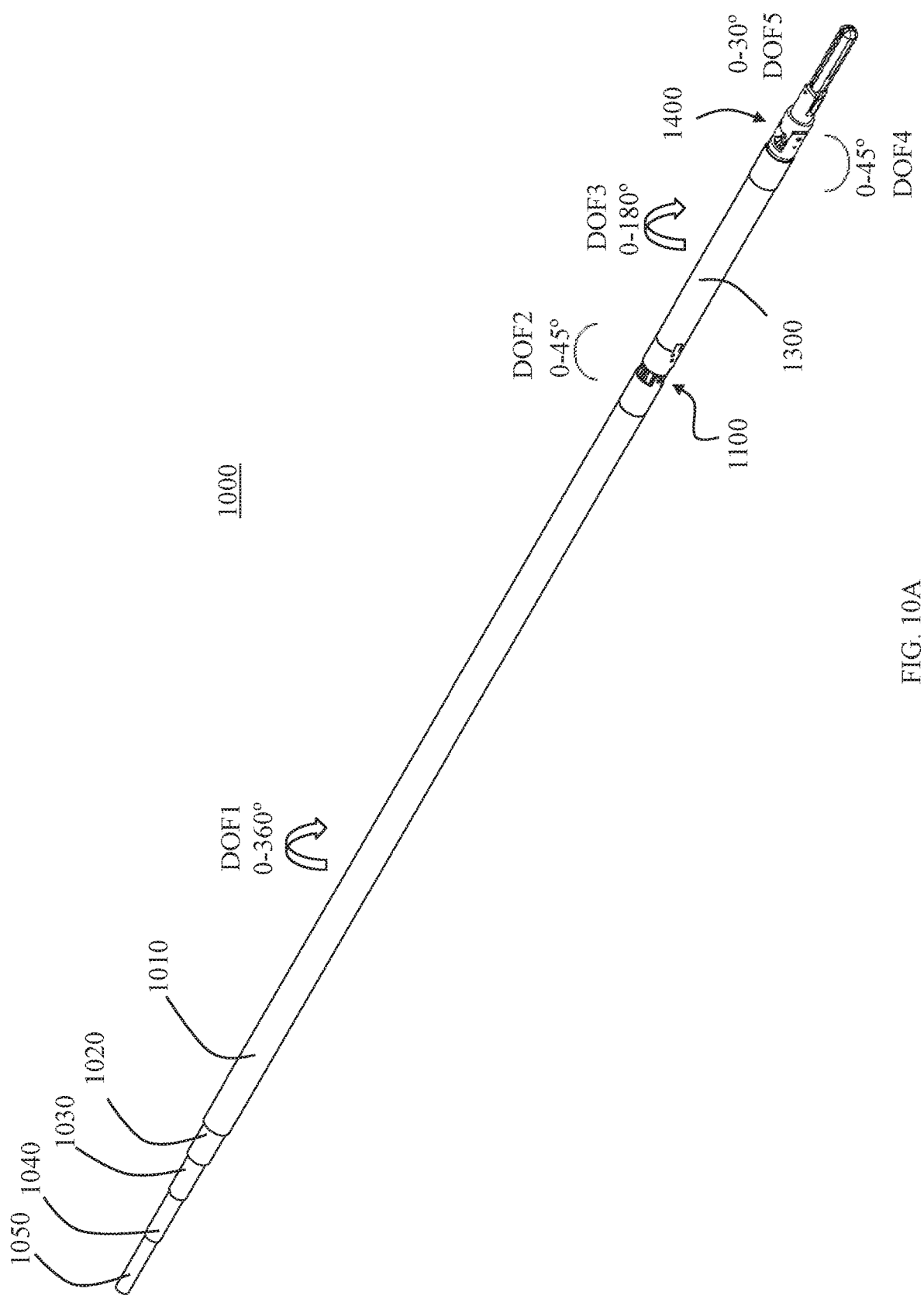
FIG. 10A is a perspective view of an arm assembly of a robotic surgical system in accordance with an alternative preferred embodiment of the present invention.
Figure 10B:
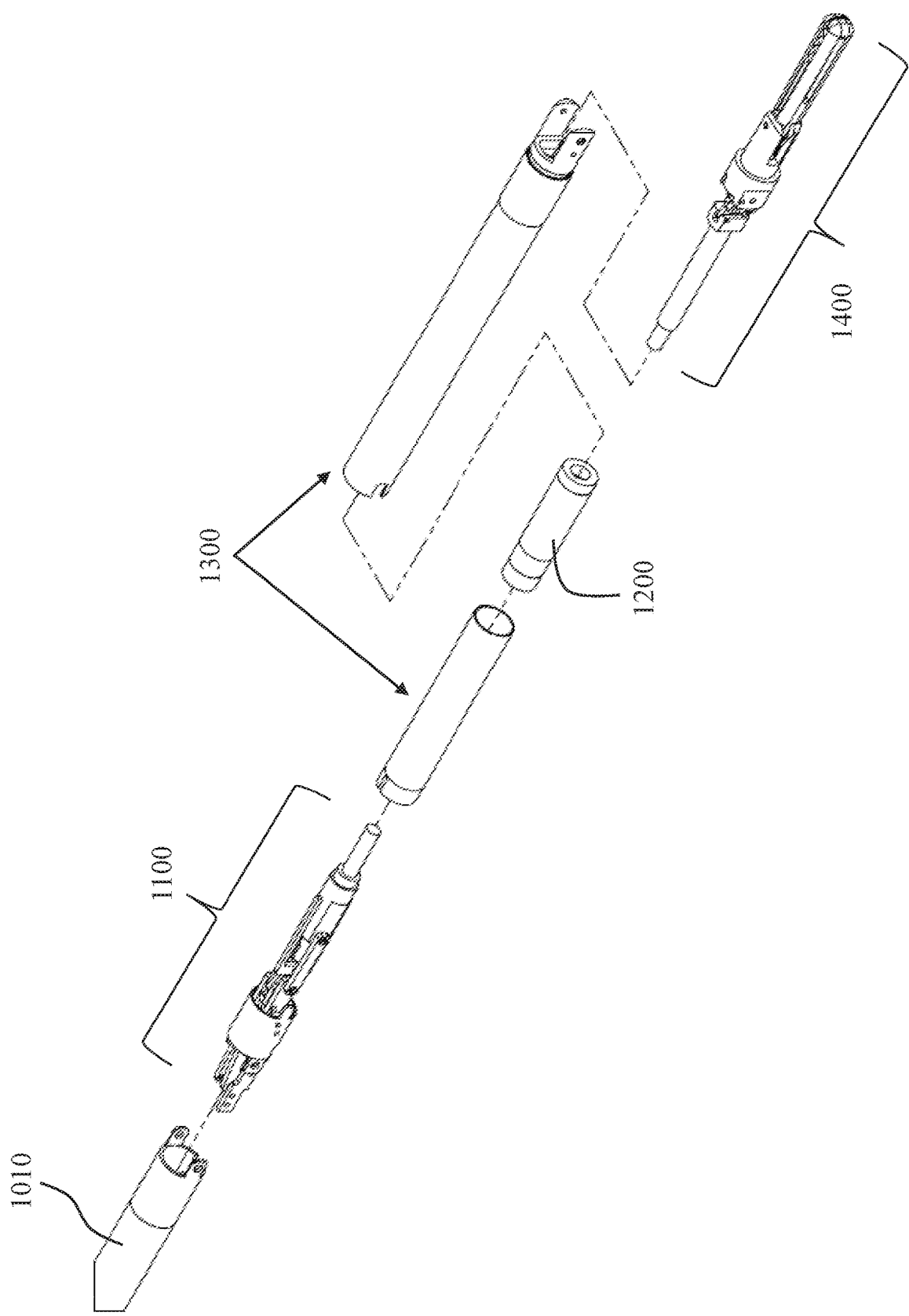
FIG. 10B is a perspective view assembly drawings of an arm assembly of a robotic surgical system in accordance with an alternative preferred embodiment of the present invention.
Figure 10C:
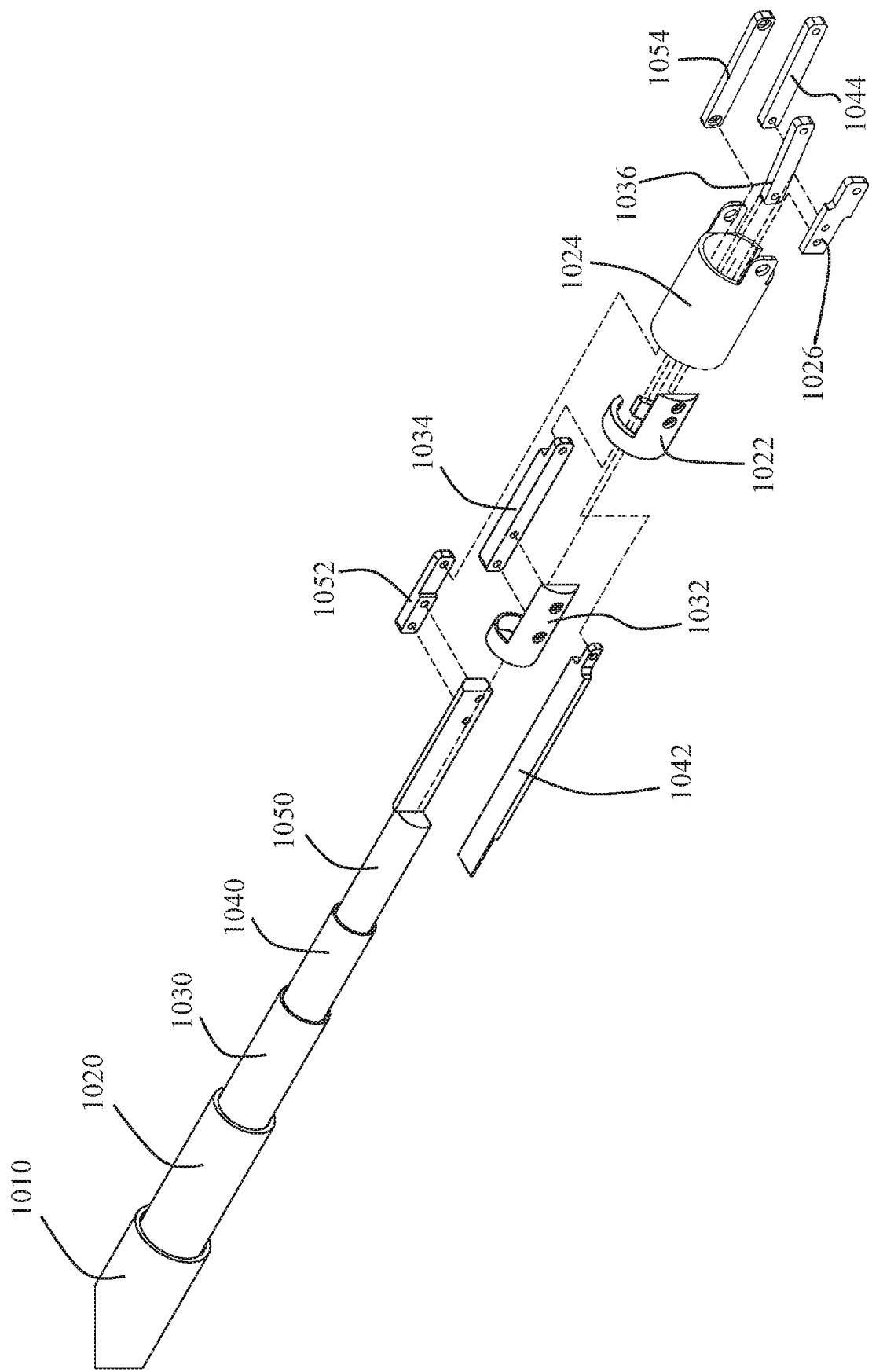
FIG. 10C is a perspective view of the actuator section of an arm assembly of a robotic surgical system in accordance with an alternative preferred embodiment of the present invention.
Figure 11:
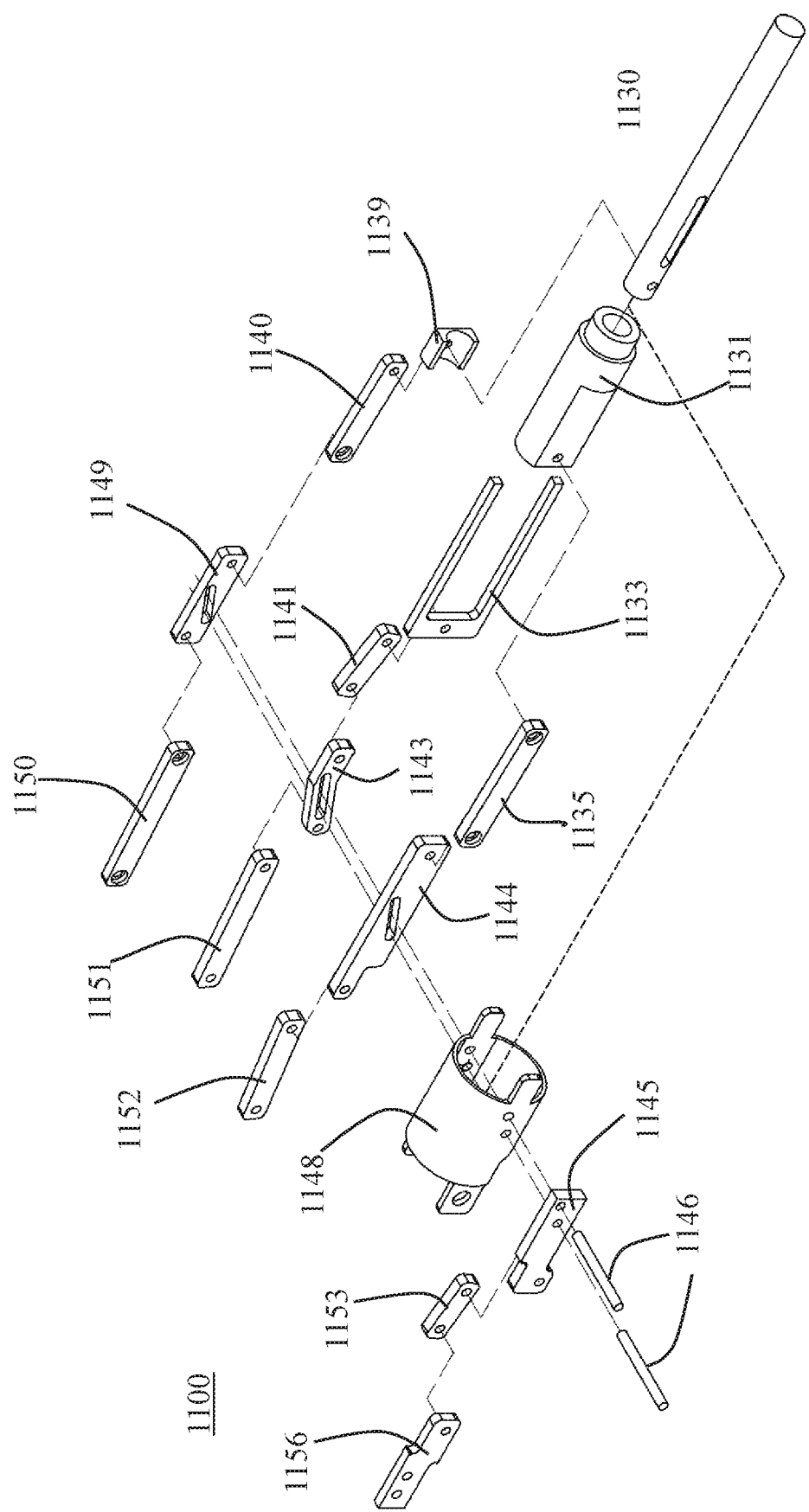

An alternative embodiment of a mechanical arm in accordance with the present invention is described with reference to FIGS. 10A-10C and FIGS. 11-14. The mechanical arm 1000 has a plurality of actuator tubes 1010, 1020, 1030, 1040, 1050 and joints or swivels 1100, 1200, 1300, 1400 that provide for movement of the mechanical arm. The structure provides five degrees of freedom as shown in FIG. 10A. The actuation tubes and mechanisms are shown in FIG. 10C. There are five actuation tubes, one for each degree of freedom: actuation tube 1010 for DOF1, actuation tube 1020 for DOF2, actuation tube 1030 for DOF5, actuation tube 1040 for DOF3 and actuation tube 1050 for DOF4. Each degree of freedom ("DOF") has an actuating tube and in most cases other elements associated with it. DOF1 is a 360 degree rotation implemented with actuation tube 1010. DOF22 is a 0-45° bending motion at joint 1100 and is controlled by actuation tube 1020, D section tube 1022, hinge joint 1024, and actuation link 1026. DOF3 is a 180° rotation implemented with actuation tube 1040, actuating rod 1042, actuating link 1044. DOF4 is implemented with actuation tube 1050, actuation links 1032 and 1052, and actuation link 1054. DOF5 is implemented with actuation tube 1030, D section tube 1032, and actuation link 1036.

Figure 1A:
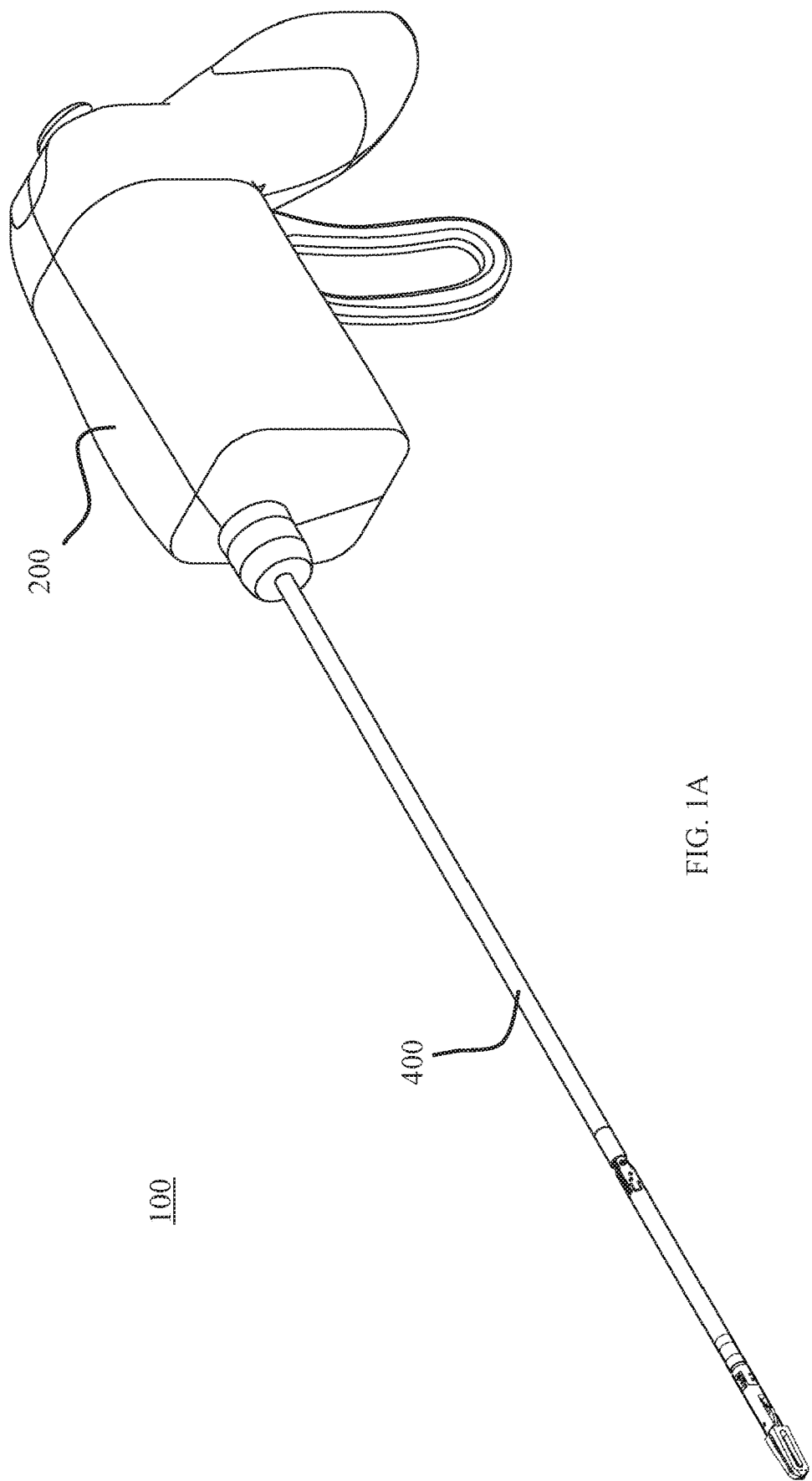
FIG. 1A is a perspective view of a robotic surgical system in accordance with a preferred embodiment of the present invention.
Figure 1B:
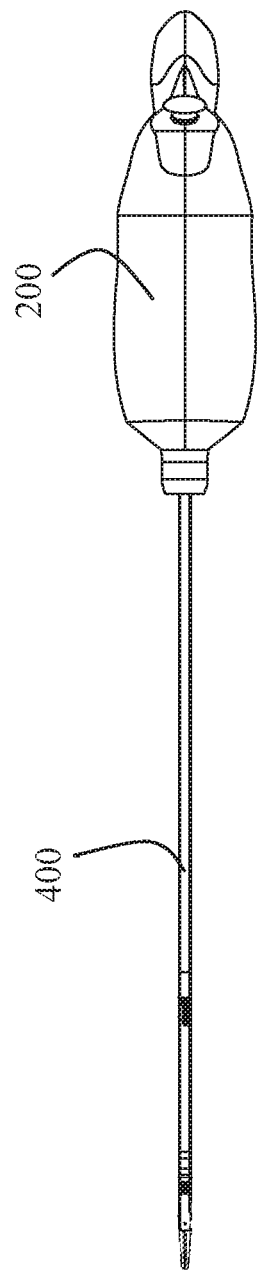
FIG. 1B is a top view of a robotic surgical system in accordance with a preferred embodiment of the present invention.
Figure 1C:
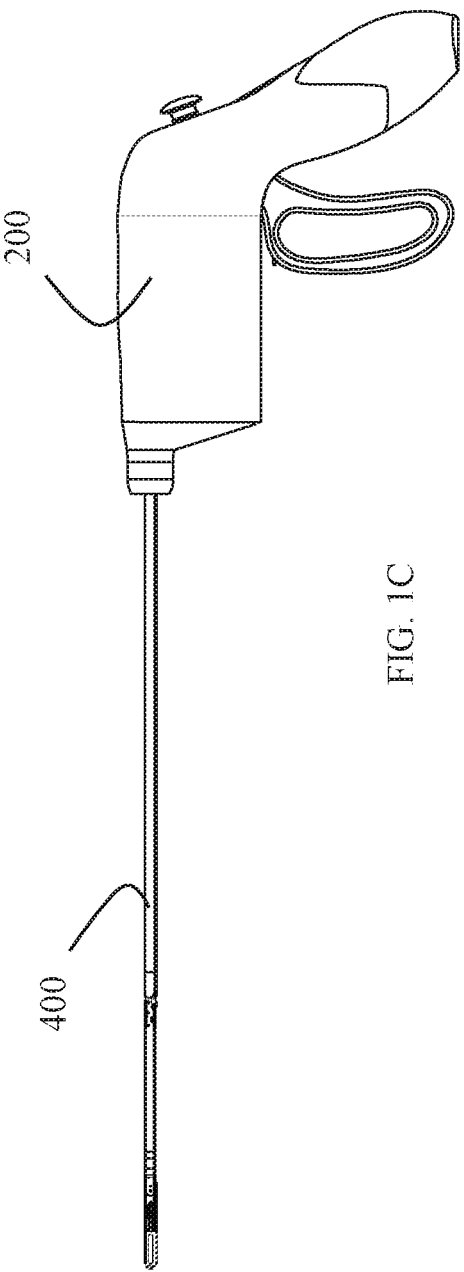
FIG. 1C is a first side view of a robotic surgical system in accordance with a preferred embodiment of the present invention.
Figure 1D:
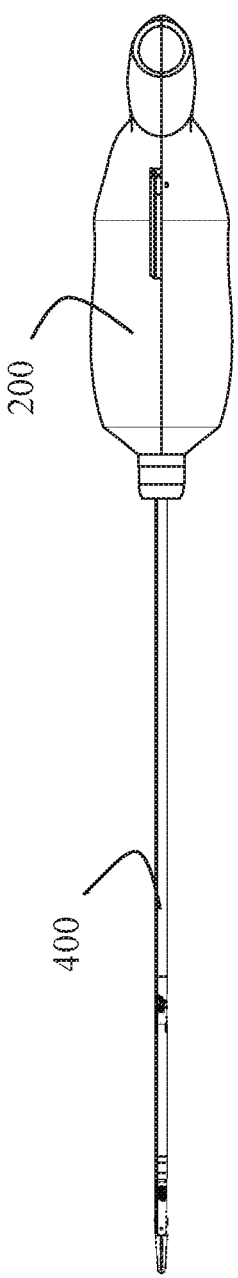
FIG. 1D is a bottom view of a robotic surgical system in accordance with a preferred embodiment of the present invention.
Figure 1E:
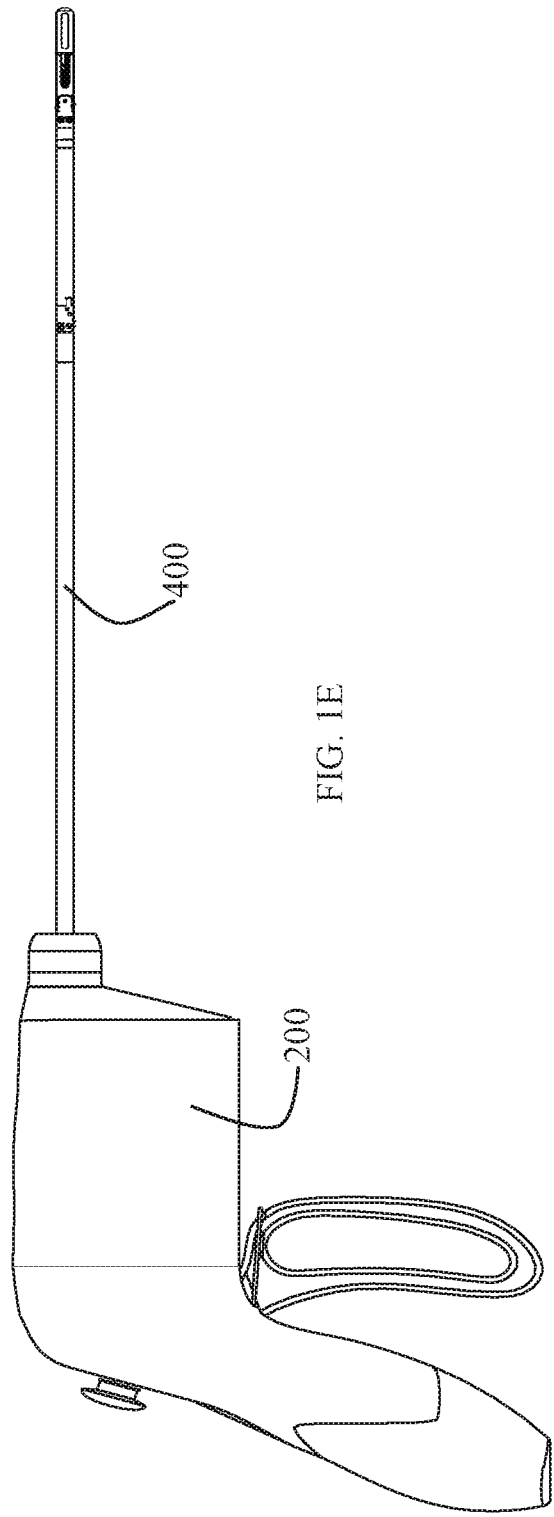
FIG. 1E is a second side view of a robotic surgical system in accordance with a preferred embodiment of the present invention.
Figure 1G:
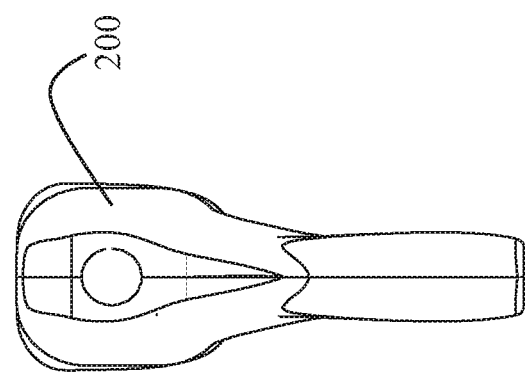
FIG. 1G is a rear end view of a robotic surgical system in accordance with a preferred embodiment of the present invention.
Figure 1F:
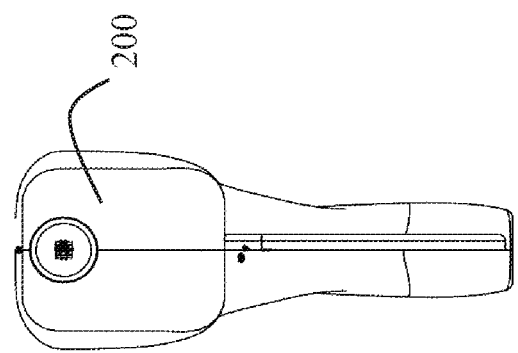
FIG. 1F is a front end view of a robotic surgical system in accordance with a preferred embodiment of the present invention.
Figure 1H:
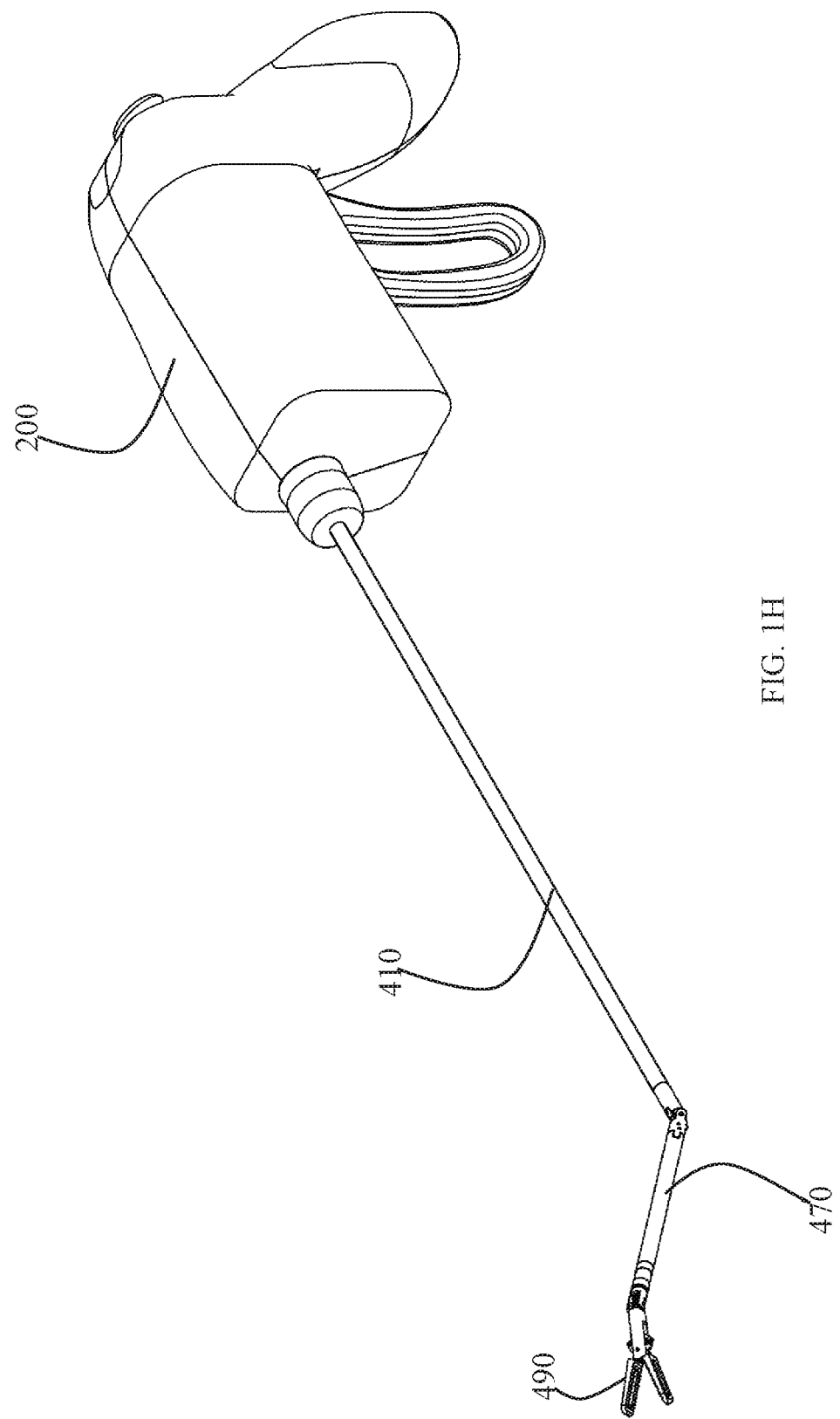
FIG. 1H is a perspective view of the robotic surgical system of FIG. 1A illustrating an alternate positioning of the arm assembly in accordance with a preferred embodiment of the present invention.
Figure 11:
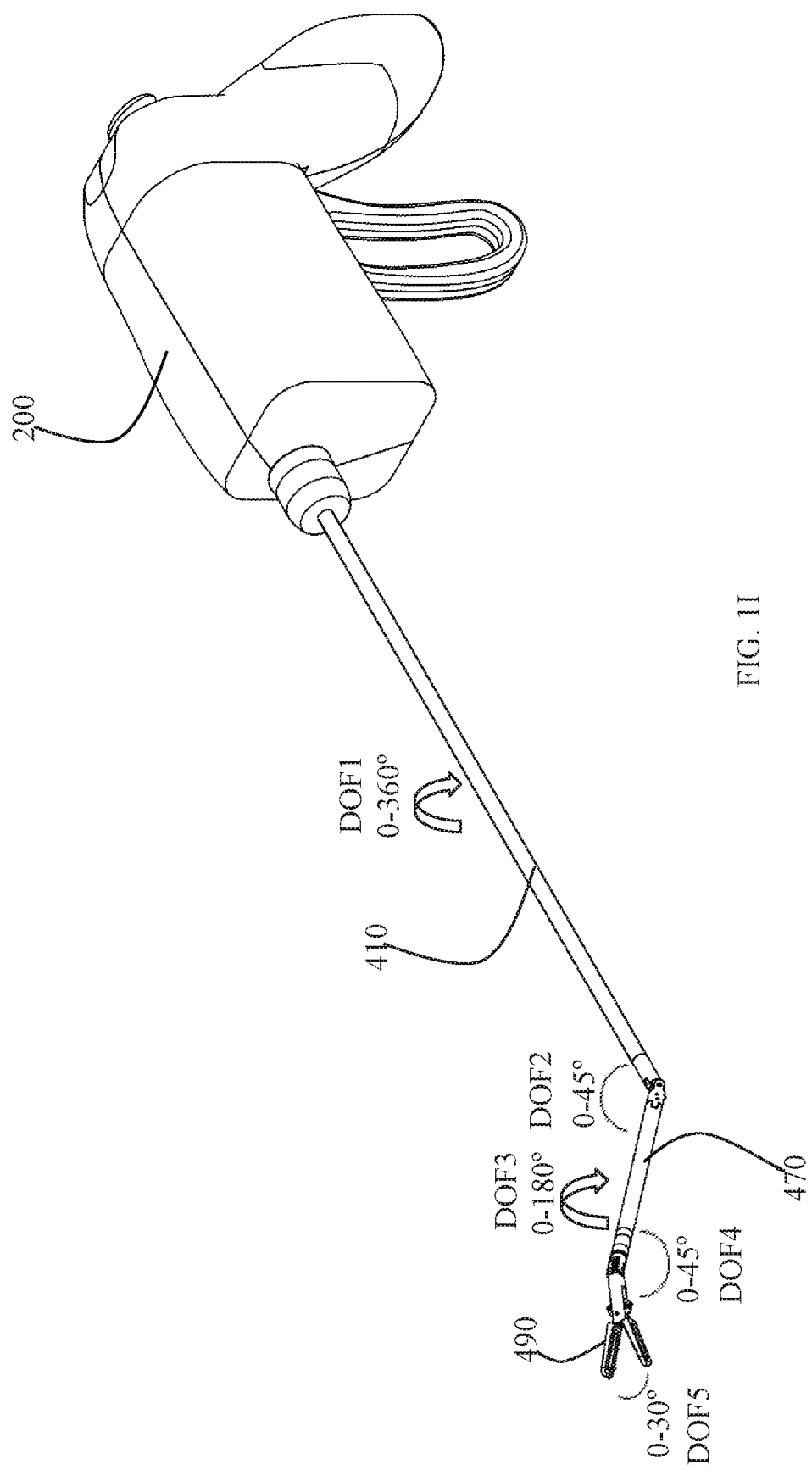
FIG. 11 is a perspective assembly view of an arm assembly illustrating a second degree of freedom of a robotic surgical system in accordance with an alternative preferred embodiment of the present invention.

FIG. 11 is an assembly drawing of Joint 2. The various parts of Joint 2 are connect to one another, for example, with pins 1146. The various component parts of Joint 2 relate to different degrees of freedom. For DOF2, actuation link 1156 connects to actuation link 1153 which connects to actuation link 1145 which connects to hinge joint 1148. For DOF3, actuation link 1151 connects to actuation link 1143, which connects to actuation link 1141 which connects to actuation link 1133. For DOF4, actuation link 1150 connects to actuation link 1149, which connects to actuation link 1140, which connects to actuation link 1139 which connects to actuation rod 1130. For DOF5, actuation link 1152 connects to actuation link 1144 which connects to actuation link 1135 which connects to actuation tube 1131.

Figure 12:
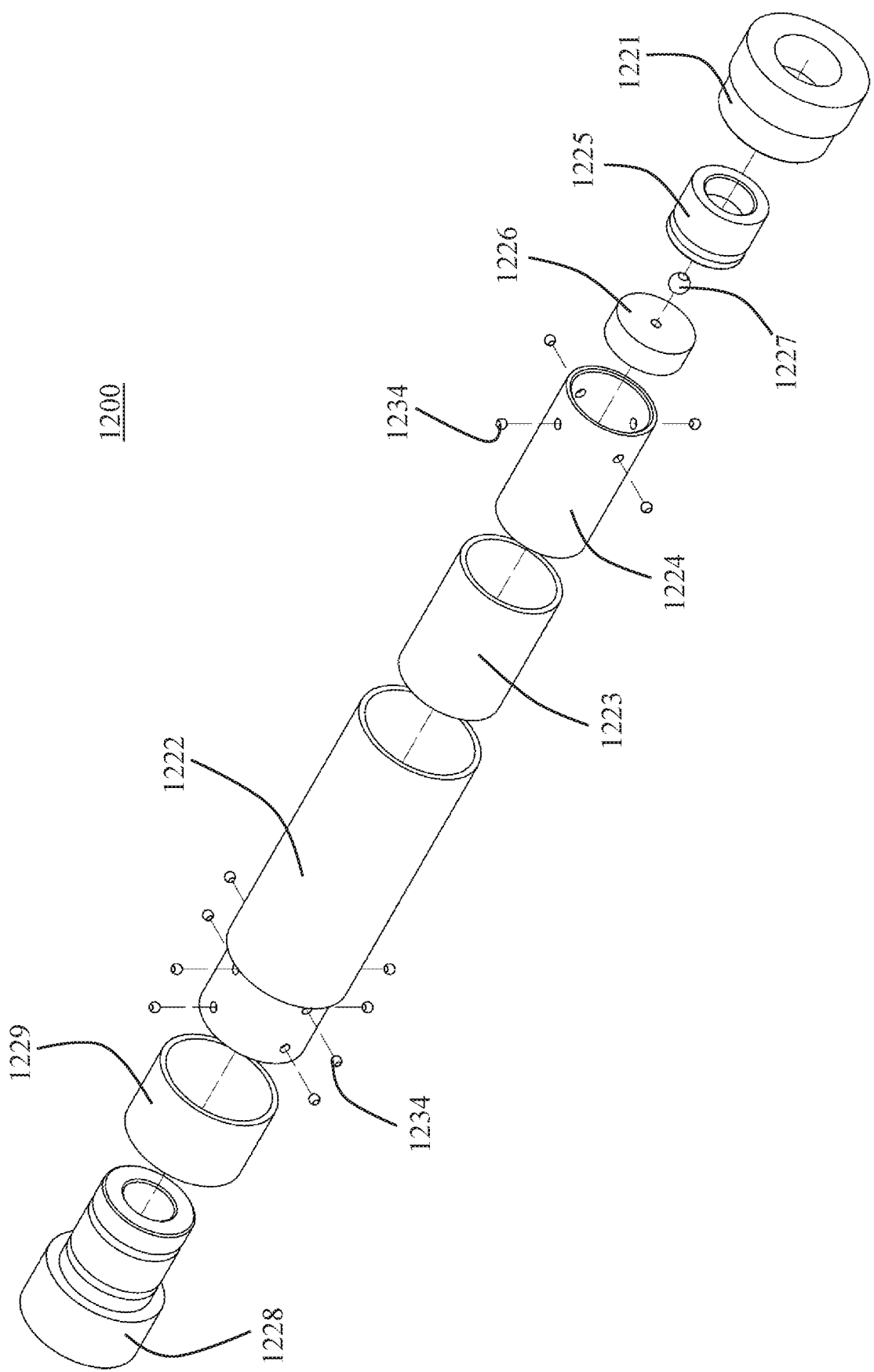
FIG. 12 is a perspective assembly view of a microswivel assembly of an arm assembly in accordance with an alternative preferred embodiment of the present invention.

FIG. 12 illustrates the structure of microswivel 1200. Has an inner microswivel and an outer microswivel. In the outer microswivel, outer tube end 1228 connects outer tube 1222 with balls 1234, which allow for rotation of the tubes relative to one another. Outer ball cover 1229 covers the balls 1234. Our tube end 1221 connects to the outer tube 1222. The inner microswivel is inside the outer microswivel and has inner tube 1224, a PFTE bearing 1226, a stainless steel ball 1227, and inner tube end 1225. The inner tube end 1225 connects to inner tube 1224 with balls 1234, which in turn are covered by inner ball cover 1223.

Figure 13:
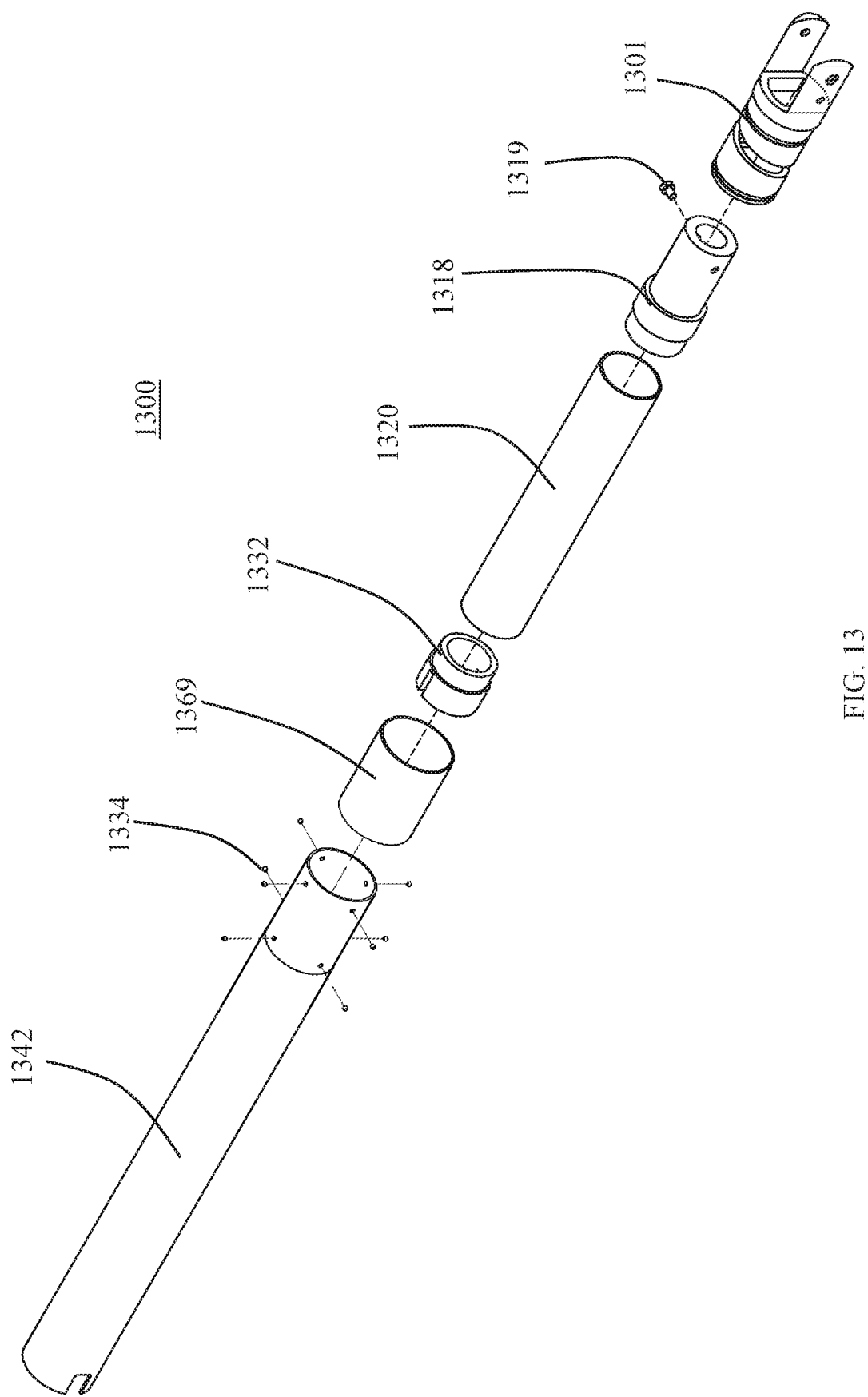
FIG. 13 is a perspective assembly view of an arm assembly illustrating a third degree of freedom of a robotic surgical system in accordance with an alternative preferred embodiment of the present invention.

FIG. 13 is an assembly drawing of Joint 3, which relates to DOF3. Joint 3 has outer tube 1342, balls 1334, ball cover 1369, actuation tube 1332, actuation tube 1320, actuation tube 1318, actuation button 1319 and helical hinge 1301.

Figure 14:
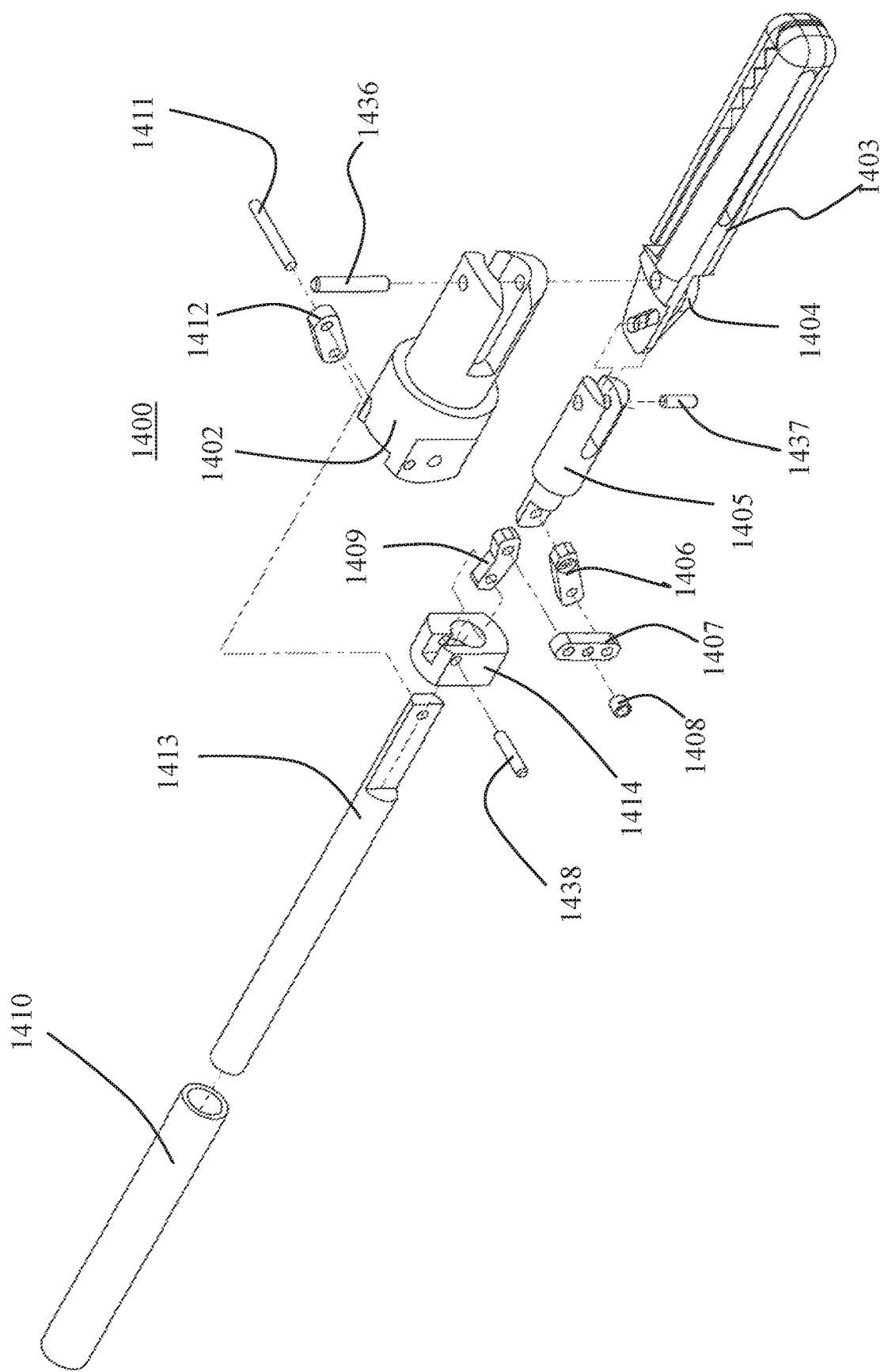
FIG. 14 is a perspective assembly view of an arm assembly illustrating fourth and fifth degrees of freedom of a robotic surgical system in accordance with an alternative preferred embodiment of the present invention.

FIG. 14 is an assembly diagram of Joints 4 and 5 which relate to DOF4 and DOF5. The structure for DOF4 includes actuation rod 1413, hinge joint 1402, actuation link 1412, and rotational pin 1411. DOF5 includes actuation tube 1410, slide block 1414 slider pin 1438, wheel bar links 1406, 1407, 1409, wheel bar spacer 1408, and actuation rod 1405. The gripper includes gripper arms 1403, 1404, and gripper pins 1436, 1437.

The robotic system of the present invention is a non-cable operating robotic surgical system. The system may be used with flexible instruments such as flexible laparoscopic attachment that may include scissors for cutting and coagulation, a needle holder, a grasper, a tissue dissector or any other instrument. One skilled in the art will recognized that the system can be used or combined with any minimally invasive instrument, including but not limited to flexible and rigid laparoscopes, thoracoscopes, cystoscopes, bronchoscopes, endoscopes and colonoscopies.

The surgeon can uses the robotic system at the operating table similar to the rigid laparoscope on the market. The robotic system will also can integrate a 3-D Optic system.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A robotic surgical system comprising:
   a hand piece comprising:
      a rigid housing having a body portion and a grip portion, said body portion having a nosepiece;
      a motor assembly within said rigid housing, said motor assembly comprising:
         a frame;
         first and second pairs of motors, each motor in each of said first and second pairs of motors having a longitudinal axis, the longitudinal axes of the first and second pairs of motors being parallel to one another, each motor of each of said first and second motors having a motor housing secured to said frame, each motor in said first pair of motors having a drive shaft extending from its motor housing parallel to its longitudinal axis and toward said nosepiece and each motor in said second pair of motors having a drive shaft extending from its motor housing parallel to its longitudinal axis and away from said nosepiece;
         a drive spool connected to the drive shaft of each motor;
         a friction drive having a spool connected to one of said drive spools by a drive band;
         a plurality of drive rods supported by said frame parallel to said plane, each of said plurality of drive rods extending across at least one of said pairs of motors;
         a plurality of secondary drive spools, each of said plurality of secondary drive spools being connected to one of said plurality of drive rods;
         a drive band connecting each secondary drive spool to one of said drive spools;
         a plurality of drive rings, each drive ring being driven by one of said plurality of drive rods; and
         control electronics electrically connected to said drive motors;
      a control mechanism connected to said control electronics and extending through an opening in said rigid housing;
      a mode control mechanism connected to said control electronics and extending through an opening in said rigid housing; and
      a connector for connecting a power source for providing power to said control electronics and said motors; and
   a mechanical arm connected to said hand piece, said mechanical arm extending through each of said drive rings and having four degrees of freedom with each of said four degrees of freedom being controlled by one of said plurality of motors, said mechanical arm comprising at least three nested actuation tubes of differing sizes, each actuation tube controlling one of said degrees of freedom of said mechanical arm, and wherein each drive ring drives one of said actuation tubes to move said mechanical arm in said degree of freedom controlled by said actuation tube.

2. A robotic surgical system according to claim 1, wherein said hand piece further comprises a mechanical trigger for controlling a fifth degree of freedom of said mechanical arm.

3. A robotic surgical system according to claim 1, wherein said hand piece further comprises a display screen connected to said control electronics for displaying operational information of said robotic surgical system.

4. A robotic surgical system according to claim 1 further comprising a disposable outer shell encasing said housing.

5. A robotic surgical system according to claim 4, wherein said disposable outer shell is formed from a flexible clear material.

6. A robotic surgical system comprising:
   a hand piece comprising:
      a rigid housing having a body portion and a grip portion, said body portion having a nosepiece;
      a motor assembly within said rigid housing, said motor assembly comprising:
         a frame;
         a first and second pairs of motors secured to said frame, each motor in each of said first and second pairs of motors having a longitudinal axis, the longitudinal axes of the first and second pairs of motors being parallel to one another, each motor in each of said first and second pairs of motors having a motor housing each motor in said first pair of motors having a drive shaft extending from its motor housing parallel to its longitudinal axis and toward said nosepiece and each motor in said second pair of motors having a drive shaft extending from its motor housing parallel to its longitudinal axis and away from said nosepiece;
         a drive spool connected to the drive shaft of each motor;
         a plurality of drive rods supported by said frame above said plurality of motors;
         a plurality of secondary drive spools, each of said plurality of secondary drive spools being connected to one of said plurality of drive rods;
         a drive band connecting each secondary drive spool to one of said drive spools;
         a plurality of drive rings, each drive ring being driven by one of said plurality of drive rods; and
         control electronics electrically connected to said drive motors;
      a control mechanism connected to said control electronics and extending through an opening in said rigid housing;
      a mode control mechanism connected to said control electronics and extending through an opening in said rigid housing; and
      a connector for connecting a power source for providing power to said control electronics and said motors; and
   a mechanical arm connected to said hand piece, said mechanical arm extending through each of said drive rings and having a-four degrees of freedom with each of said four degrees of freedom being controlled by one of said plurality of motors, said mechanical arm comprising at least three nested actuation tubes of differing sizes, each actuation tube controlling one of said degrees of freedom of said mechanical arm, and wherein each drive ring drives one of said actuation tubes to move said mechanical arm in said degree of freedom controlled by said actuation tube.

7. A robotic surgical system according to claim 6, wherein said mechanical arm comprises:
   a secondary drive spool on said mechanical arm for controlling one of said four degrees of freedom of said mechanical arm; and
   a drive band connecting said secondary drive spool on said mechanical arm to one of said drive spools.

8. A robotic surgical system according to claim 6, wherein said hand piece further comprises a mechanical trigger for controlling a fifth degree of freedom of said mechanical arm.

9. A robotic surgical system according to claim 6, wherein said hand piece further comprises a display screen connected to said control electronics for displaying operational information of said robotic surgical system.

10. A robotic surgical system according to claim 6 further comprising a disposable outer shell encasing said housing.

\* \* \* \* \*